(12) United States Patent
Windum

(10) Patent No.: US 11,318,257 B2
(45) Date of Patent: May 3, 2022

(54) DRUG DELIVERY DEVICE WITH CLUTCH FEATURE

(71) Applicant: Novo Nordisk A/S, Bagsvaerd (DK)

(72) Inventor: Jesper Peter Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 160 days.

(21) Appl. No.: 16/461,590

(22) PCT Filed: Dec. 1, 2017

(86) PCT No.: PCT/EP2017/081100
§ 371 (c)(1),
(2) Date: May 16, 2019

(87) PCT Pub. No.: WO2018/100124
PCT Pub. Date: Jun. 7, 2018

(65) Prior Publication Data
US 2019/0366008 A1    Dec. 5, 2019

(30) Foreign Application Priority Data

Dec. 1, 2016 (EP) ..................................... 16201777

(51) Int. Cl.
*A61M 5/315* (2006.01)
*A61M 5/20* (2006.01)
(Continued)

(52) U.S. Cl.
CPC ...... *A61M 5/31551* (2013.01); *A61M 5/2033* (2013.01); *A61M 5/2422* (2013.01);
(Continued)

(58) Field of Classification Search
CPC .......... A61M 5/31558; A61M 5/31543; A61M 2005/2403; A61M 2005/407;
(Continued)

(56) References Cited

U.S. PATENT DOCUMENTS 7,008,399 B2    3/2006   Larsen et al.
RE41,956 E     11/2010   Klitgaard et al.
(Continued)

FOREIGN PATENT DOCUMENTS

CN    104271184       1/2015
CN    104334216 A     2/2015
(Continued)

*Primary Examiner* — Emily L Schmidt
*Assistant Examiner* — Joshua Parker Reddington
(74) *Attorney, Agent, or Firm* — Wesley Nicolas

(57) ABSTRACT

A drug delivery device comprising or adapted to receive a drug-filled cartridge, comprising a piston rod adapted to be rotated by a drive member to thereby move the piston rod distally during expelling, dose setting means allowing a user to simultaneously set a dose amount to be expelled, and a releasable locking mechanism adapted to rotationally lock the drive member relative to the housing during dose setting. The device further comprises release means actuatable between a dose setting mode and an expelling mode, wherein the locking mechanism is released when the release means is actuated from a dose setting mode to an expelling mode.

13 Claims, 18 Drawing Sheets

US 11,318,257 B2
Page 2

(51) Int. Cl.
  *A61M 5/24* (2006.01)
  *A61M 5/31* (2006.01)

(52) U.S. Cl.
  CPC .... *A61M 5/31541* (2013.01); *A61M 5/31568* (2013.01); *A61M 2005/202* (2013.01); *A61M 2005/2485* (2013.01); *A61M 2005/3126* (2013.01); *A61M 2205/50* (2013.01); *A61M 2205/581* (2013.01)

(58) Field of Classification Search
  CPC .. A61M 2005/2411; A61M 2005/2414; A61M 5/31568; A61M 2005/202; A61M 5/31585; A61M 5/31551; A61M 5/31541; A61M 5/31553; A61M 5/31561; A61M 5/31548; A61M 5/3155; A61M 5/31555
  See application file for complete search history.

(56) References Cited

U.S. PATENT DOCUMENTS

| | | | |
|---|---|---|---|
| 8,579,867 B2 | 11/2013 | Harms et al. |
| 8,911,411 B2 | 12/2014 | Nielsen |
| 8,920,383 B2 | 12/2014 | Enggaard et al. |
| 9,114,211 B2 | 8/2015 | Enggaard et al. |
| 9,492,619 B2 | 11/2016 | Raab |
| 9,675,760 B2 | 6/2017 | Butler et al. |
| 9,766,599 B2 | 9/2017 | Draper et al. |
| 10,376,644 B2 | 8/2019 | Krusell et al. |
| 10,737,035 B2 | 8/2020 | Bilton |
| 2009/0318865 A1 | 12/2009 | Moller et al. |
| 2010/0114025 A1 | 5/2010 | Moller |
| 2011/0054412 A1 | 3/2011 | Eich et al. |
| 2012/0245532 A1 | 9/2012 | Frantz et al. |
| 2014/0142511 A1 | 5/2014 | Gilmore et al. |
| 2015/0080811 A1 | 3/2015 | Wieselblad |
| 2016/0015903 A1 | 1/2016 | Madsen et al. |
| 2016/0235924 A1 | 8/2016 | Soerensen et al. |
| 2016/0256631 A1 | 9/2016 | Soerensen et al. |
| 2016/0287807 A1 | 10/2016 | Madsen et al. |
| 2016/0296710 A1 | 10/2016 | Bainton et al. |
| 2018/0064880 A1 | 3/2018 | Kiilerich |
| 2019/0336698 A1 | 11/2019 | Klitmose |

FOREIGN PATENT DOCUMENTS

| | | | |
|---|---|---|---|
| CN | 105658264 B | 9/2019 | |
| EP | 730876 A2 | 9/1996 | |
| EP | 1351732 | 1/2001 | |
| EP | 2453951 A1 | 5/2012 | |
| JP | 2010521275 A | 6/2010 | |
| JP | 2016514554 A | 5/2016 | |
| WO | 04078241 | 9/2004 | |
| WO | 2006/128794 | 12/2006 | |
| WO | 2010052275 A2 | 5/2010 | |
| WO | 2010097125 A1 | 9/2010 | |
| WO | 2013010884 A1 | 1/2013 | |
| WO | 2014128156 A1 | 8/2014 | |
| WO | 2014139916 A1 | 9/2014 | |
| WO | 2014161952 A1 | 10/2014 | |
| WO | 2014187814 A1 | 11/2014 | |
| WO | 2015032778 A1 | 3/2015 | |
| WO | 2015055642 A1 | 4/2015 | |
| WO | WO-2015055641 A1 * | 4/2015 | .......... A61M 39/105 |
| WO | WO-2015075136 A1 * | 5/2015 | ........ A61M 5/31568 |
| WO | 2016001298 A1 | 1/2016 | |
| WO | 2016001307 A1 | 1/2016 | |
| WO | 2016135237 A1 | 9/2016 | |
| WO | 2016180873 A1 | 11/2016 | |
| WO | 02053214 A1 | 7/2019 | |

* cited by examiner

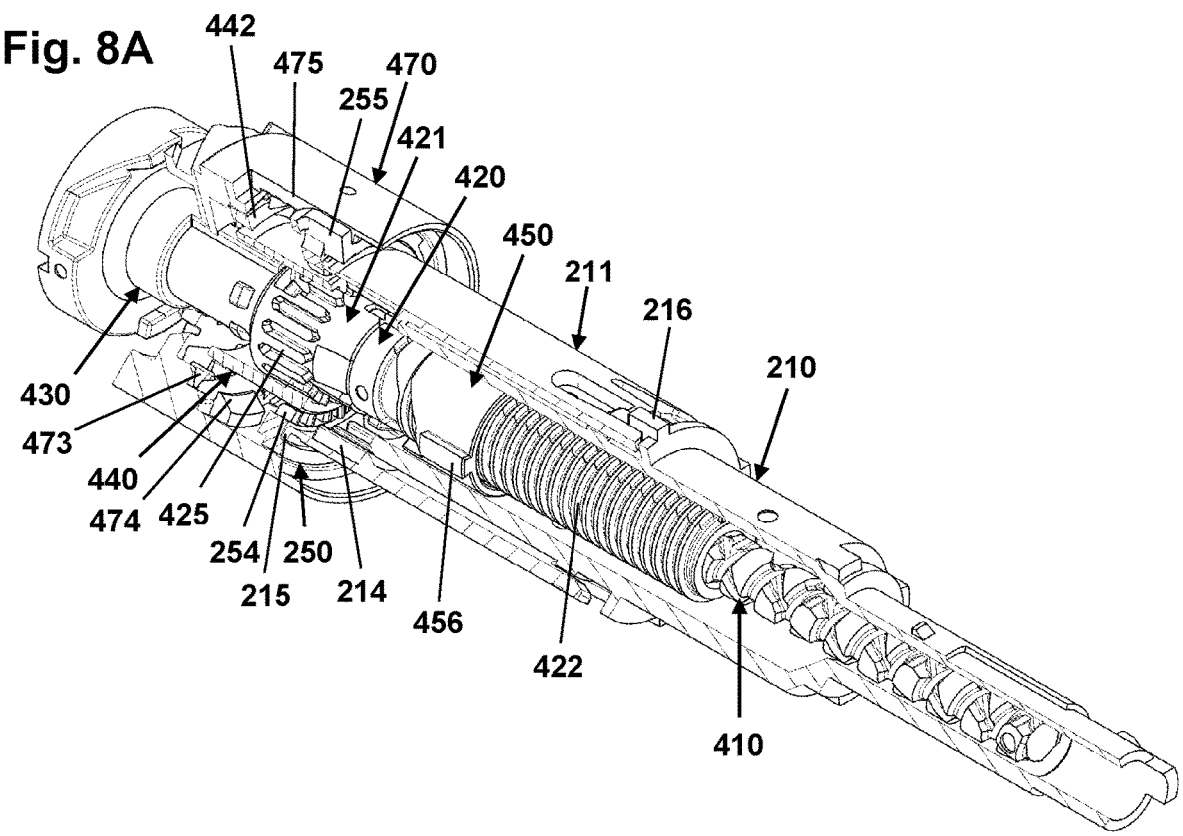
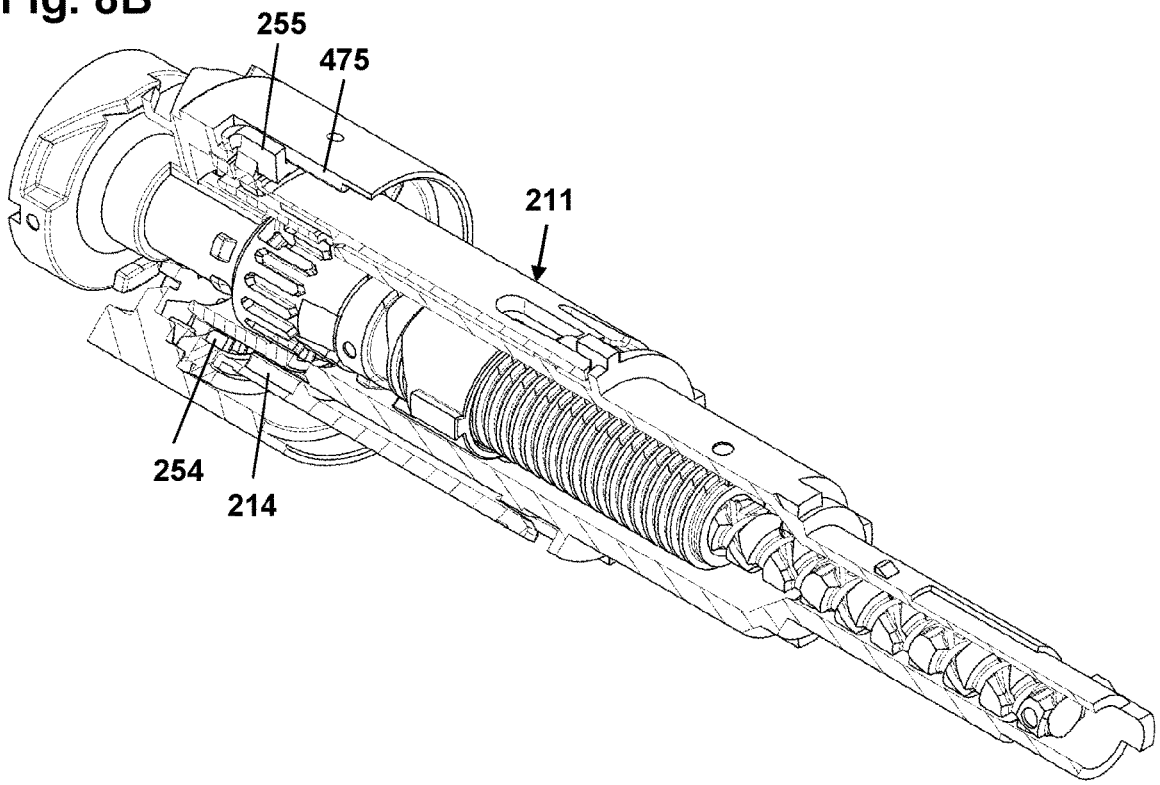

DRUG DELIVERY DEVICE WITH CLUTCH FEATURE

CROSS-REFERENCE TO RELATED APPLICATIONS

This application is a 35 U.S.C. § 371 National Stage application of International Application PCT/EP2017/081100 (published as WO 2018/100124), filed Dec. 1, 2017, which claims priority to European Patent Application 16201777.6, filed Dec. 1, 2016, the contents of all above-named applications are incorporated herein by reference.

The present invention generally relates to drug delivery devices adapted to receive a drug filled cartridge and expel a dose therefrom.

BACKGROUND OF THE INVENTION

In the disclosure of the present invention reference is mostly made to the treatment of diabetes, however, this is only an exemplary use of the present invention.

Drug delivery devices have greatly improved the lives of patients who must self-administer drugs and biological agents. Drug delivery devices may take many forms, including simple disposable devices that are little more than an ampoule with an injection means to relatively complex pre-filled disposable devices which may even be spring-driven, or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results is a misleading picture of the injection history and thus a misleading basis for the medical personnel's decision making with respect to future medication. Accordingly, it may be desirable to automate the logging of ejection information from medication delivery systems.

Correspondingly, a number of drug delivery devices with a dose monitoring/acquisition feature has been provided, see e.g. in US 2009/0318865, WO 2010/052275 and U.S. Pat. No. 7,008,399. However, most devices of today are without it. A durable spring-driven drug delivery device with a proximally arranged logging module is disclosed in WO 2014/187814 and US 2016/0235924, the latter disclosing an axially moveable clutch member.

In order to reliably detect a given expelled dose it is important that the drug delivery device per se is capable of precisely and reliably expel a given set dose. An example of a contemporary disposable spring-driven drug delivery device is disclosed in WO 2014/161952, and a corresponding durable spring-driven drug delivery device is disclosed in US 2011/0054412.

Having regard to the above, it is a general object of the present invention to provide a drug delivery device which cost-effectively and reliably allows a set dose of drug to be expelled. The device may be provided with a spring-driven expelling mechanism and may be in the form of a durable device adapted to be used with pre-filled cartridges.

It is a further general object of the present invention to provide a drug delivery device and system as well as components therefore which cost-effectively and reliably allows detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device comprising or adapted to receive a drug-filled cartridge is provided. The device comprises a housing, a piston rod adapted to engage and axially displace a piston in a loaded cartridge in a distal direction to thereby expel a dose of drug from the cartridge. The device further comprises a transmission member defining an axis, a drive spring coupled to the transmission member, a drive member in engagement with the piston rod and adapted to be rotated by the transmission member to thereby move the piston rod distally during expelling, and dose setting means allowing a user to simultaneously set a dose amount to be expelled and strain the drive spring correspondingly by rotation of the transmission member, the dose setting means comprising a dose setting member which during dose setting is rotationally coupled to the transmission member and adapted to rotate in a first direction to set a dose. The device also comprises a releasable ratchet mechanism allowing the dose setting member to be rotated in the first direction to a set rotational position, a releasable clutch mechanism adapted to rotationally lock the drive member relative to the housing during dose setting, and release means actuatable between a dose setting mode and an expelling mode. The clutch mechanism comprises a relative to the housing axially non-moveable clutch member, and a relative to the housing rotationally non-moveable locking member, wherein during dose setting and dose expelling the clutch member is rotationally locked to the drive member. The transmission member is actuatable between a dose setting state in which it is allowed to rotate relative to the clutch member, and an expelling state in which it is rotationally coupled to the clutch member, and the locking member is actuatable between a dose setting state in which it is in rotationally locked engagement with the clutch member, and an expelling state in which it is rotationally decoupled from the clutch member. When the release means is actuated from the dose setting mode to the expelling mode, then the transmission member is actuated from its dose setting state to its expelling state, the locking member is actuated from its dose setting state to its expelling state, and the ratchet mechanism is released, whereby the strained drive spring is allowed to rotate the transmission member and the drive member and thereby move the piston rod distally.

By this arrangement an axially non-moveable clutch member can be used as a "platform" for controlling coupling and uncoupling of separate locking and transmission members, this allowing improved operational control when shifting between dose setting and dose expelling mode in a spring-driven drug delivery device.

Further by the locking arrangement it can be prevented to a high degree that the drive member is rotated and thereby the piston rod moved unintentionally, e.g. when a dose is being set or the device is being stored, this assuring to a high degree that an expelled dose corresponds to a given set dose.

In an exemplary embodiment the transmission member and the locking member are moved axially when actuated between the dose setting state and the expelling state, e.g. by means of axial movement of the release means. The transmission member and the locking member may be axially locked but rotationally free relative to each other.

In an exemplary embodiment the locking member is in splined engagement with the clutch member in the dose setting state, and the transmission member is in splined engagement with the clutch member in the expelling state. The splines may be incrementally "synchronized" with the ratchet mechanism such that the splines on the clutch member are positioned rotationally corresponding to the splines on the transmission member, this allowing for clutch engagement without undesired rotation of the engaging components.

The transmission member may at least partly engage the clutch member before the locking member has been actuated to its expelling state. The clutch member may be coupled to the housing via a uni-directional ratchet mechanism.

In a further exemplary embodiment a drug delivery device as described above is provided with a cartridge holder coupled to the housing and adapted to receive and hold a drug-filled cartridge, as well as a coupling mechanism allowing the piston rod to be moved in a proximal direction, this allowing a new cartridge to be received. The coupling mechanism may be actuatable between an operational state in which the piston rod can be moved in the distal direction by rotation of the clutch member, and a loading state in which the piston rod can be moved in the proximal direction.

In an exemplary embodiment the drive member is actuatable between an operational state in which the drive member is rotationally locked to the clutch member, and a loading state in which the drive member is rotationally decoupled from the clutch member, this allowing the drive member to rotate as the piston rod is moved in the proximal direction. The drive member may be arranged to be moved axially when actuated between the operational state and the loading state.

The coupling mechanism may comprise a coupling member adapted to engage a proximal end portion of a cartridge, e.g. the circumferential proximal rim, the coupling member being moveable between a distal loading position in which the piston rod can be moved in the proximal direction, and a proximal operational position in which the piston rod can be moved in the distal direction by rotation of the clutch member. The coupling member may be biased towards its distal position by a spring. The coupling member and the drive member may be axially locked but rotationally free relative to each other, this allowing the biasing spring to move the drive member out of engagement with the clutch member when a cartridge is removed from the cartridge holder.

The cartridge holder may be of the front-loaded type actuatable between a receiving state in which a cartridge can be inserted and received in a proximal direction, and a holding state in which an inserted cartridge is held in an operational position. The coupling mechanism may be actuated between the loading state and the operational state when the cartridge holder is actuated between the receiving state and the holding state with a mounted cartridge. In this way the expelling mechanism will be rendered non-operational with no mounted cartridge. Alternatively, the coupling mechanism may be controlled by the cartridge holder when actuated between the receiving state and the holding state.

The cartridge holder may alternatively be of the traditional rear-loaded type which can be detached from the device main housing, this allowing a cartridge to be inserted in a distal direction into the cartridge holder before the cartridge holder is reattached to the device main housing. As for the front-loaded cartridge holder type the coupling mechanism may be operated by the cartridge or the cartridge holder.

In specific embodiments the drug delivery devices as described above is provided with dose logging circuitry adapted to determine an amount of expelled drug, the determination comprising determining, directly or indirectly, the amount of rotation of the transmission member relative to the housing during expelling of an amount of drug.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein FIG. 1 show a front-loaded drug delivery device with a drug cartridge mounted FIG. 8A shows in a first partial cut-away view a portion of the expelling mechanism in a dose setting mode, FIG. 8B shows the expelling mechanism of FIG. 8A in a dose expelling mode.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. When it is defined that members are mounted axially free to each other it generally indicates that they can be moved relative to each other, typically between defined stop positions whereas when it is defined that members are mounted rotationally free to each other it generally indicates that they can be rotated relative to each other either freely or between defined stop positions. The terms "assembly" and "subassembly" do not imply that the described components necessarily can be assembled to provide a unitary or functional assembly or subassembly during a given assembly procedure but is merely used to describe components grouped together as being functionally more closely related.

Figure 1:
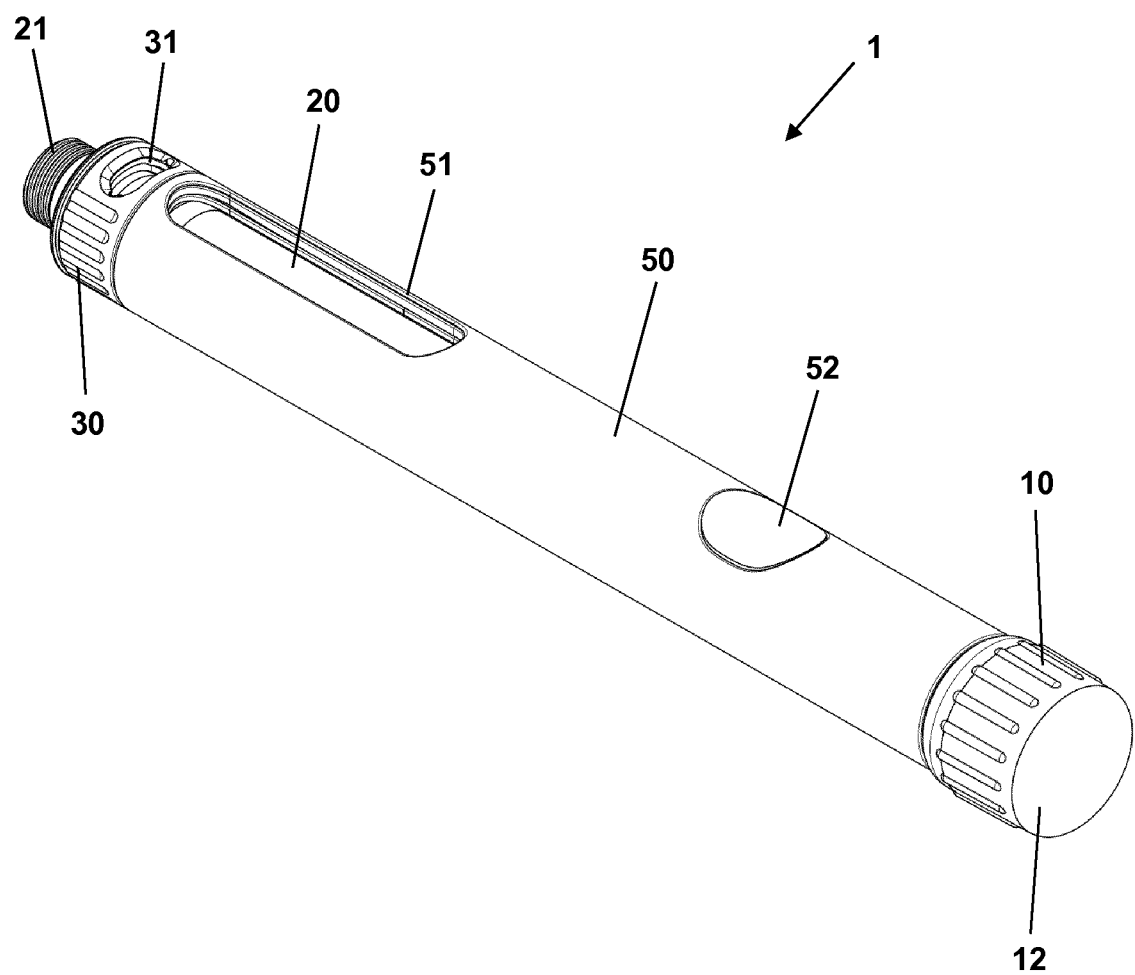
Figure 6A:
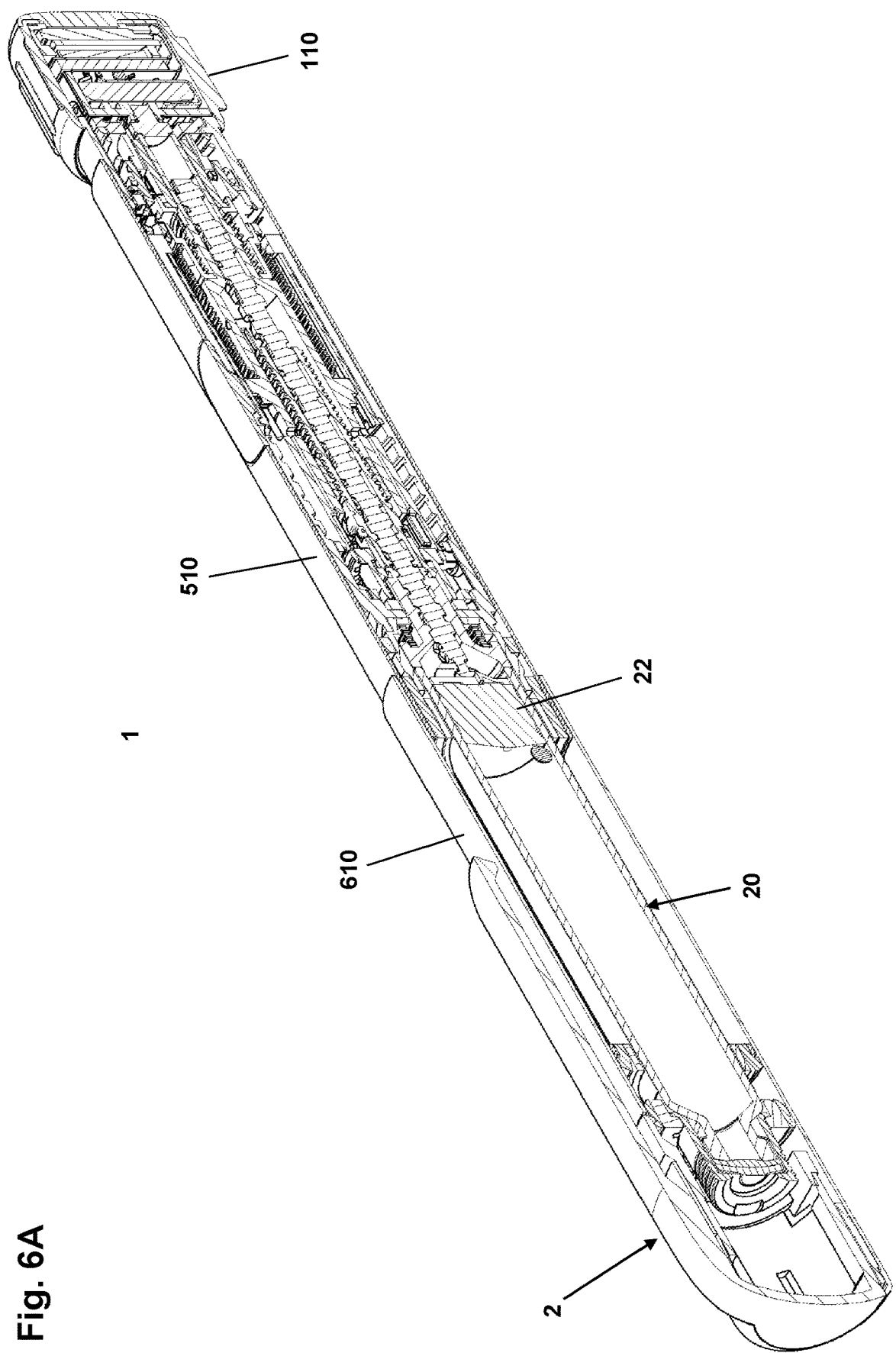
FIG. 6A shows in a cross-sectional front-isometric view the device of FIG. 1.

Referring to FIG. 1 a pen-formed drug delivery device 1 will be described. More specifically, the pen device 1 of FIG. 1 comprises a cap part 2 (see FIG. 6A) and a main part having a unitary housing 50. The drug delivery device comprises an expelling assembly arranged in the proximal portion of the housing and a cartridge holder assembly arranged in the distal portion of the housing. A proximal-most rotatable combined dose setting and release member (or "button") 10 serves to manually set a desired dose of drug shown in display window 52, which can then be expelled when the combined dose setting and release button is actuated by being moved distally when the user applies a force on the proximal-most button surface 12. The button may be adapted to fully or partly house electronic circuitry allowing a set and/or expelled dose of drug to be determined. Determined dose related data may be transmitted to an external receiver and/or displayed, e.g. on a display viewable through a transparent button end cover 12. The cartridge holder assembly is adapted to receive and retain a drug-filled transparent cartridge 20 provided with a distal needle-penetrable septum and a coupling means 21 for a needle assembly, the housing comprising an opening 51 allowing the content of the cartridge to be inspected. The cartridge may for example contain an insulin, a GLP-1 or a growth hormone formulation. The device is designed to be loaded by the user with a new cartridge through a distal receiving opening in the cartridge holder assembly, the cartridge being provided with a piston 22 (see FIG. 6A) driven by a piston rod forming part of the expelling mechanism. The distal opening is opened and closed by rotation of a distal ring member 30 comprising an opening 31 allowing the content of the distal-most portion of the cartridge to be inspected. Although FIG. 1 discloses a front-loaded drug delivery device, aspects of the present invention can also be incorporated in drug delivery devices comprising a traditional removable rear-loaded cartridge holder.

Figure 2:
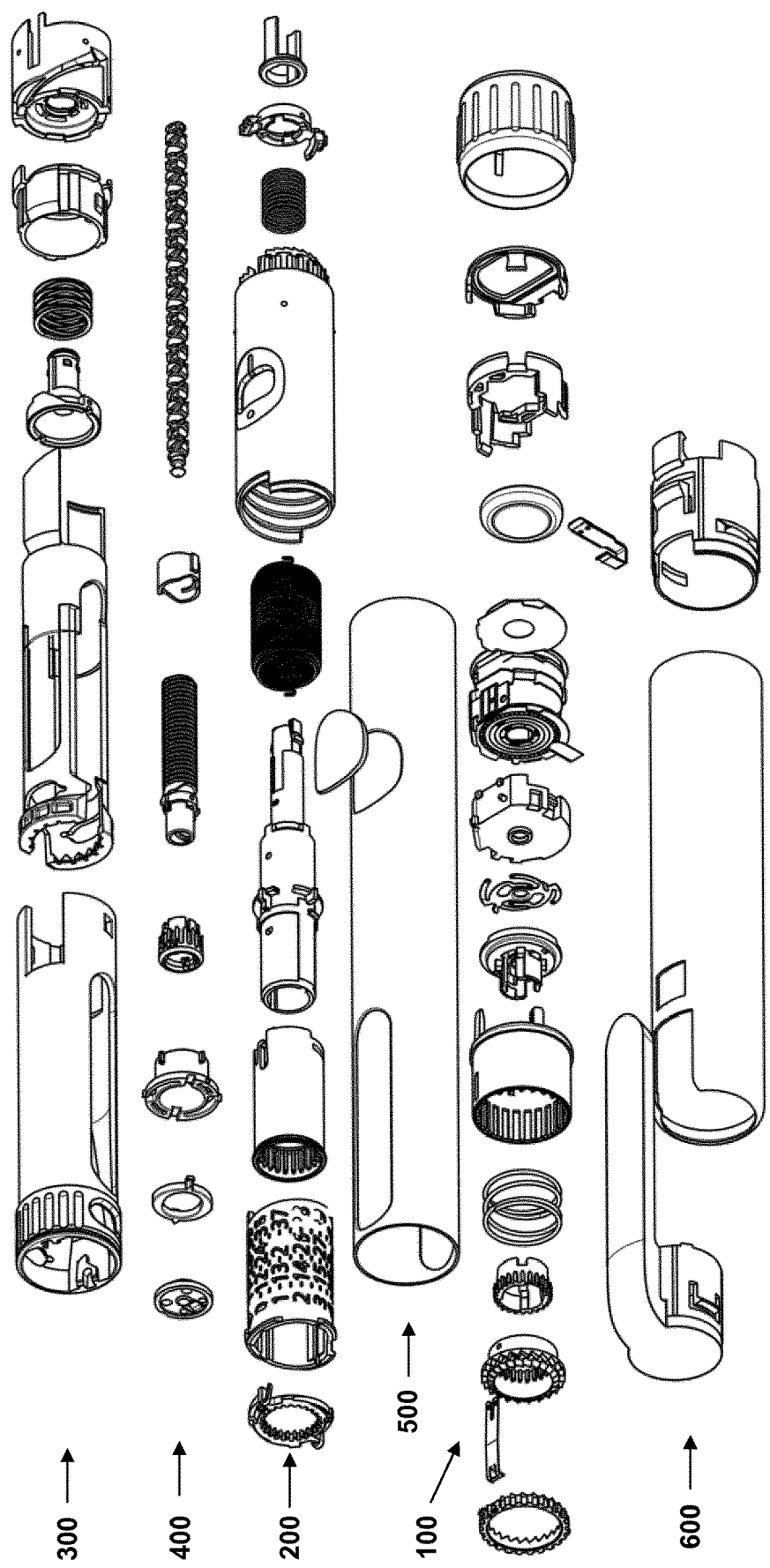
FIG. 2 shows in an exploded view the components of the drug delivery device of FIG. 1.

FIG. 2 shows in exploded views the pen-formed drug delivery device 1 shown in FIG. 1. As aspects of the invention relate to the working principles of such a pen, an exemplary embodiment of a complete pen mechanism and its features will be described, most of which are merely illustrative examples of features and designs adapted to work with and support the aspects of the present invention. The pen will be described as comprising three main assemblies: a dose setting and logging assembly 100 (or just dose setting assembly), an engine assembly 200, and a cartridge holder and drive assembly 300 with a cartridge holder sub-assembly and a drive sub-assembly 400, as well as an outer housing assembly 500 and a cap assembly 600. Although the assemblies are described as functional units, some of the functionality is realized only when the assemblies are mounted to each other to form a pen-formed drug delivery device. With reference to FIGS. 3A, 3B, 4A, 4B, 5A and 5B the different components and their structural and functional relationship will be described in greater detail.

Figure 3A:
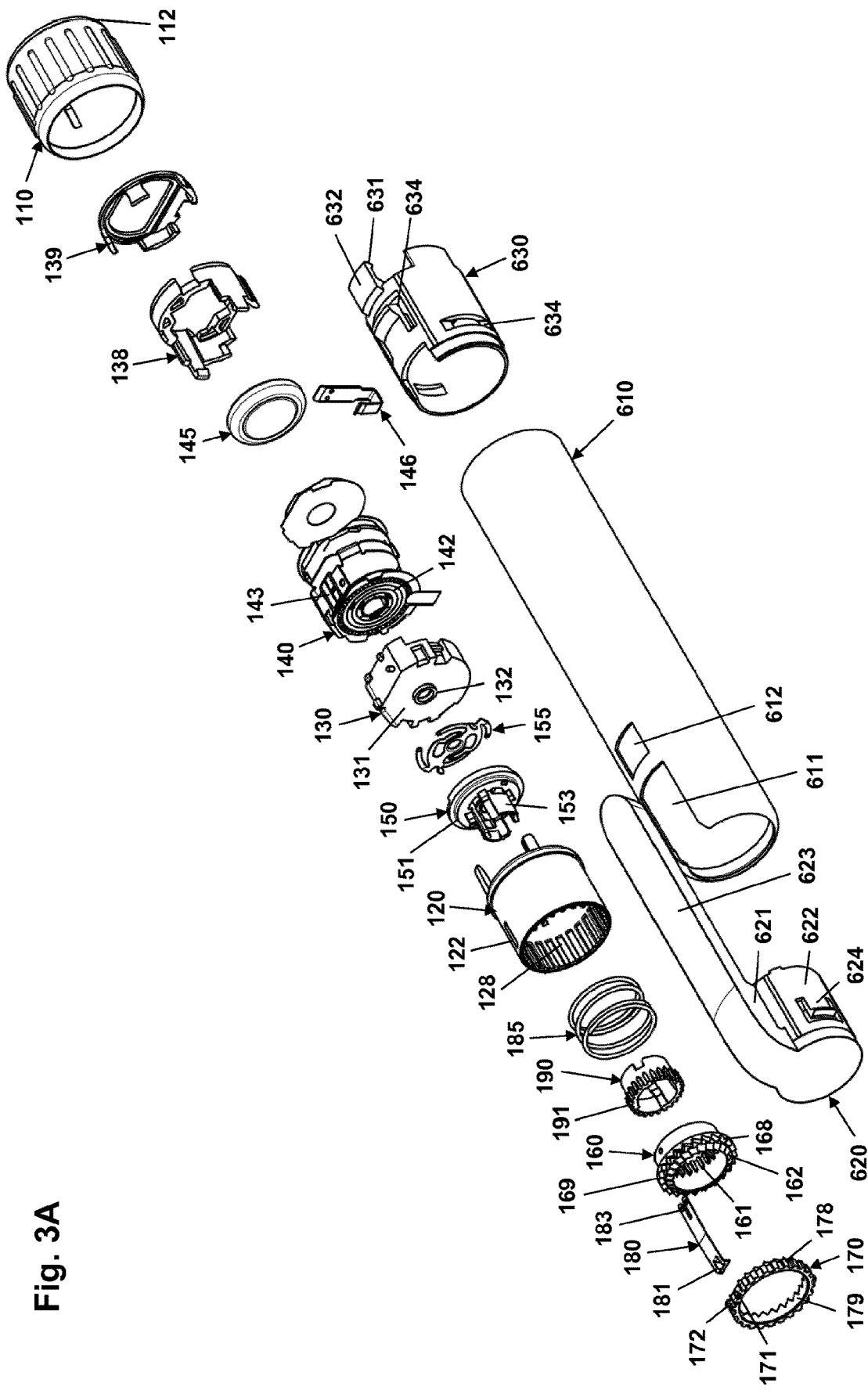
FIG. 3A shows in a front-isometric view a first group of components of the device of FIG. 2.
Figure 3B:
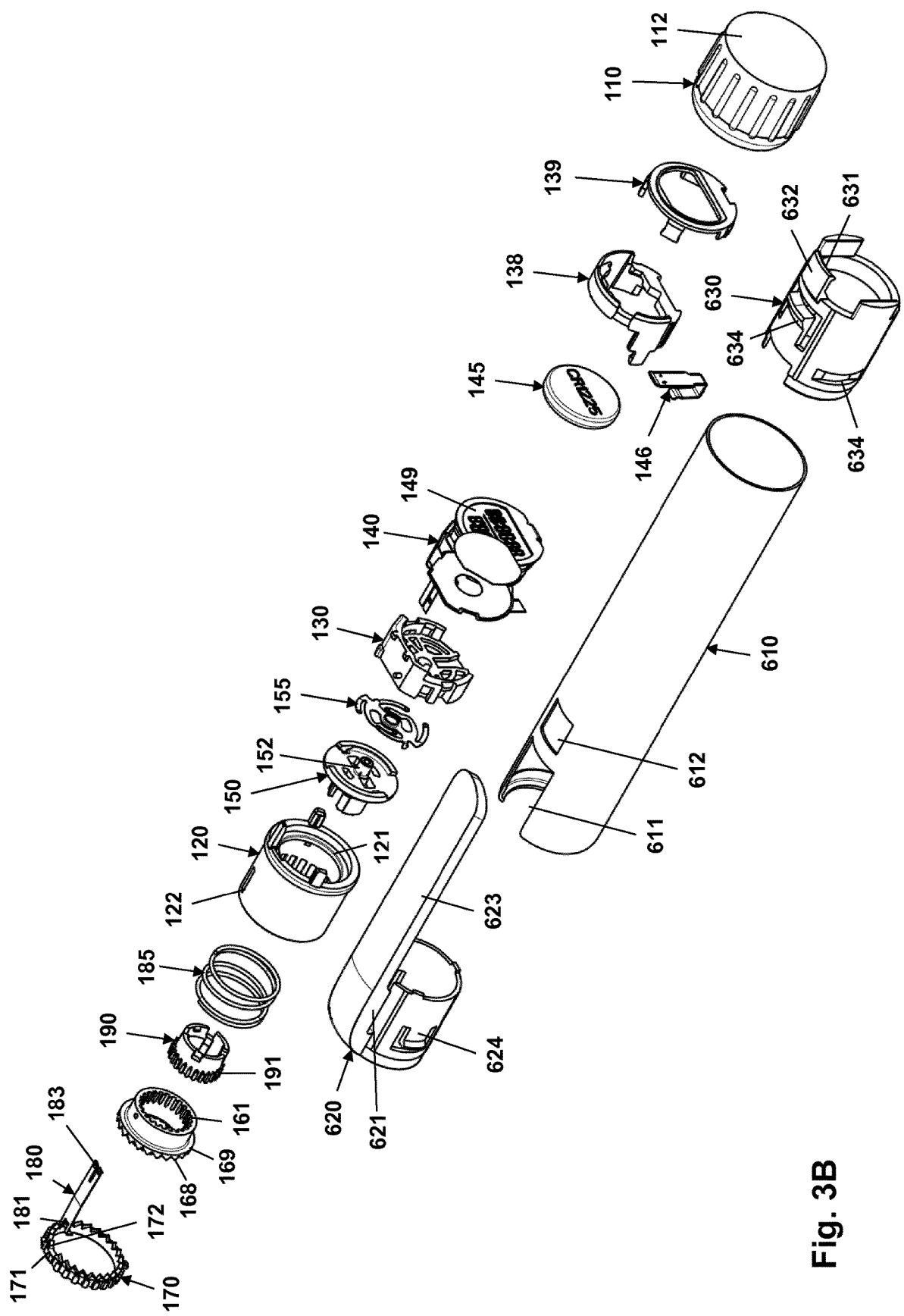
FIG. 3B shows in a rear-isometric view the first group of components of FIG. 3A.

More specifically and referring to FIGS. 3A and 3B, the dose setting assembly 100 comprises a housing portion, an electronic logging module assembly and a ratchet sub-assembly. The housing portion is formed from a proximal tubular dose setting and release button member 110 (or dose button for short) closed at the proximal end with a transparent window 112, and a distal tubular skirt member 120 having an interior circumferential flange 121 in the vicinity of the proximal end. The skirt member comprises an inner array of axially oriented distally facing splines 128 as well as a pair of opposed axially oriented guide slots 122. On the distal circumferential edge an array of distally facing teeth 125 (not shown) is arranged and adapted to engage the end-of-dose control member (see below). When assembled the two housing members form a logging compartment proximally of the circumferential flange 121 and a ratchet compartment distally of the circumferential flange.

The logging module assembly comprises a housing member 130 having a distal mounting surface 131 with a central opening 132, a flexible PCB 140 folded in a multi-layered stack, a battery 145 and battery clip 146, a housing lid 138, and an LCD frame 139. On the PCB electronic circuitry components are mounted, e.g. micro-controller, LCD 149, display driver, memory and wireless communication means.

The PCB comprises a disc-formed sensor portion 142 adapted to be mounted on the housing distal mounting surface 131, e.g. by adhesive means, the sensor portion comprising a plurality of arc-formed discreet contact areas forming the stationary first portion of a rotary sensor adapted to determine the amount of rotation of the transmission member during out-dosing (see below). The PCB further comprises a laterally facing mode switch array 143 having a dose setting mode, an intermediate mode and an expelling mode, this as described in greater detail in EP 16157986.7 [NN 150094]. In the shown embodiment the housing member 130, the housing lid 138 and the LCD frame 139 are assembled by snap connections. Apart from the sensor portion 142 the PCB 140 and the thereon mounted electronic components are arranged in the interior of the housing thereby forming a logging module.

The moving second portion of the rotary sensor is formed by a flexible contact disc 155 comprising a plurality of flexible contact arms adapted to be in rotational sliding engagement with the sensor contact areas. The contact disc 155 is adapted to be attached to the proximal surface of a disc-formed carrier member 150, the carrier member comprising a circumferential distally-facing edge portion 151 adapted to be positioned onto the circumferential flange 121 of the skirt member 120, a proximal tubular extension 152 adapted to be received in the housing central opening 132, as well as a distal connector tube portion 153 adapted to engage and lock non-moveable to the release member 190 (see below) as well as the proximal end of the transmission tube 210 (see below).

In addition to the rotary sensor the flexible contact disc 155 and the PCB sensor portion 142 also forms an end-of-dose switch actuated by the end-of-dose trigger member 270 (see below).

The ratchet sub-assembly comprises a tubular ratchet member 160, a ring-formed drive-lift control member 170, a mode switch arm 180, a tubular release member 190 and a helical ratchet spring 185.

The ratchet member 160 has a tubular body portion with an inner surface provided with a plurality of longitudinally arranged splines 161 adapted to slidingly engage corresponding splines on the drive tube release member. The ratchet member comprises a distally-facing surface on which an inner circumferential array of ratchet teeth structures 162 there by way of example, 24 teeth) is arranged around the central opening, each tooth having a triangular configuration with an inclined ratchet surface and a stop surface oriented perpendicularly to the housing member cross-sectional plane, the ratchet teeth being configured to interface with the corresponding ratchet teeth on the engine housing member (see below) to thereby provide a one-way ratchet. The ratchet member 160 further comprises an outer circumferential flange 169 with a second array there by way of example, 24 teeth) of distally-facing ratchet teeth structures 168, each tooth having a configuration with a "more inclined" lift surface and a "less inclined" drive surface.

The drive-lift control member 170 is configured as a ring-formed member having an outer circumferential surface with a plurality of longitudinally arranged splines 178 adapted to interface with the dose setting member splines 128, as well as a plurality of proximally-facing drive-lift teeth 179 arranged on the proximal circumferential edge, each tooth having a triangular form with a less inclined drive surface and a more inclined lift surface adapted to engage the corresponding drive-lift surfaces on the ratchet member 160. The control member further comprises a pair of opposed guiding projections 172 adapted to be received in the skirt guide slots 122, as well as a peripheral connecting structure 171 adapted to engage and mount the distal end 181 of the mode switch arm 180.

The tubular release member 190 comprises an outer array of outer splines 191 adapted to slidingly engage the corresponding splines 161 on the ratchet member 160. The release member further comprises (snap) locking means allowing it to be mounted fixedly (i.e. axially and rotationally locked) to the distal connector tube portion 153 of the carrier member 150. The mode switch arm 180 comprises a distal end 181 adapted to be attached to the control member and a proximal end 183 with a pair of contact points adapted to slidingly engage the PCB mode switch array 143 to shift the switch between the different modes. When mounted in the skirt member the mode switch arm is guided in a cut-out in the skirt flange. The ratchet spring 185 is adapted to be arranged between and engage the skirt flange 121 and the outer circumferential flange 169 of the ratchet member to thereby bias the axially moveable ratchet member into engagement with the control member. When the dose button is moved distally to release a set dose the ratchet spring 185 also serves as a dose button return spring.

When assembled and in combination with the engine housing member (see below) the ratchet arrangement provides what can be considered a releasable one-way ratchet, the drive arrangement allowing a dose to be set in increments corresponding to the ratchet teeth by rotating the dose button in a first direction, the lift arrangement providing that a set dose can be reduced (or "dialed down") when the dose button is rotated in an opposed second direction. Such a ratchet arrangement is described in greater detail in EP2016/053965. By providing a slight inclination on the ratchet drive surfaces the ratchet will be lifted when the maximum dose has been set, this providing an over-torque safety mechanism as described in EP application 16186501.9.

During assembly the ratchet sub-assembly members are first mounted in the skirt member, the members being held in place via the control member 170 engaging the skirt guide slots 122, the mode switch arm extending proximally out the skirt. Next the carrier member with the mounted contact disc 155 is mounted by snapping into engagement with the release member 170, this securing both members on each side of the skirt flange 121. Next the preassembled logging module is positioned to engage the contact disc respectively the mode switch arm. As the final step the button member 110 is mounted and attached to the skirt member 120 by e.g. welding. In this way a self-contained dose setting assembly 100 comprises an electronic logging module and a ratchet sub-assembly is provided.

In an alternative embodiment the logging module can be dispensed with and a "dummy" module being mounted, this providing a pen device having the same functionality but without the logging feature.

Figure 4A:
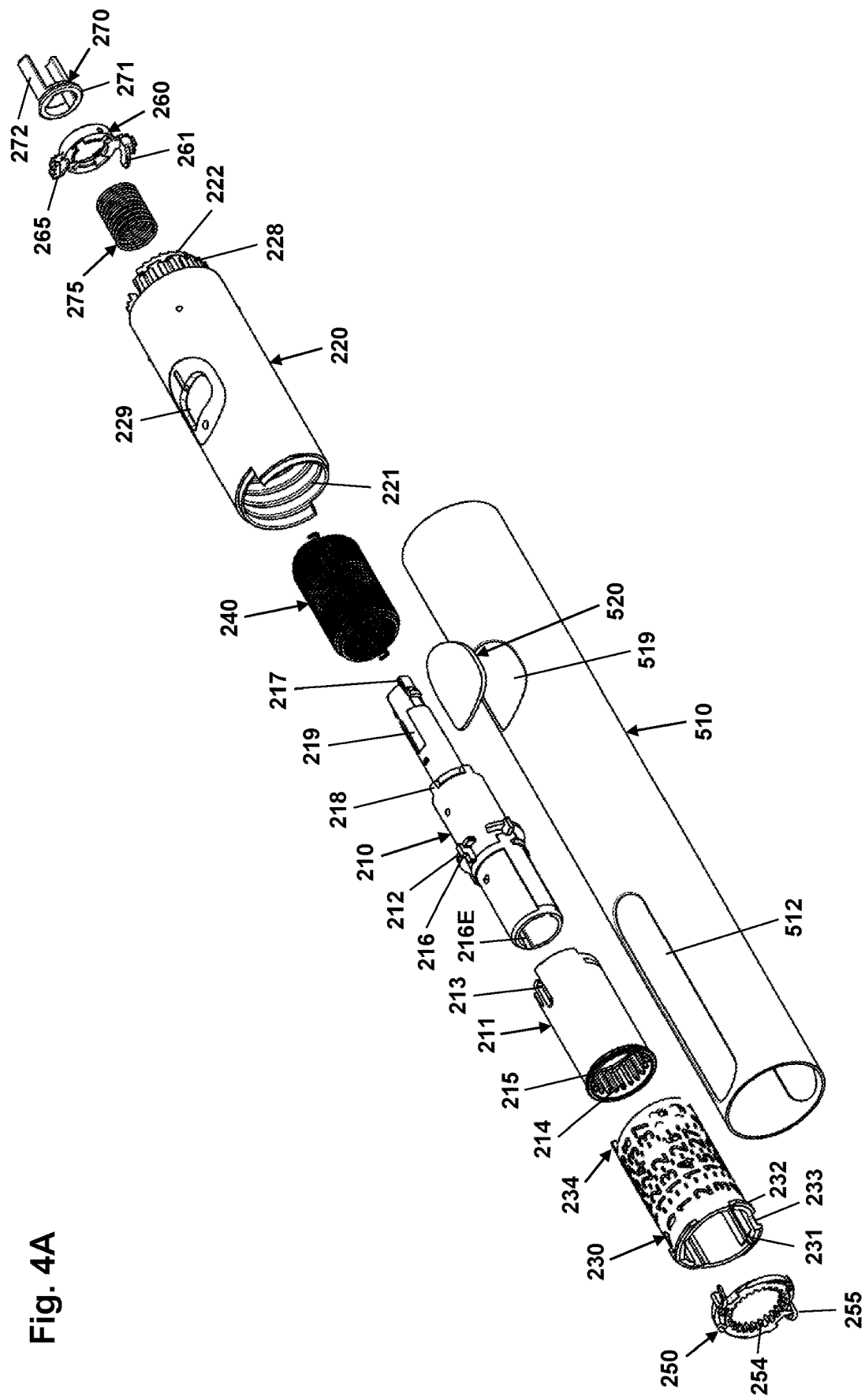
FIG. 4A shows in a front-isometric view a second group of components of the device of FIG. 2.
Figure 4B:
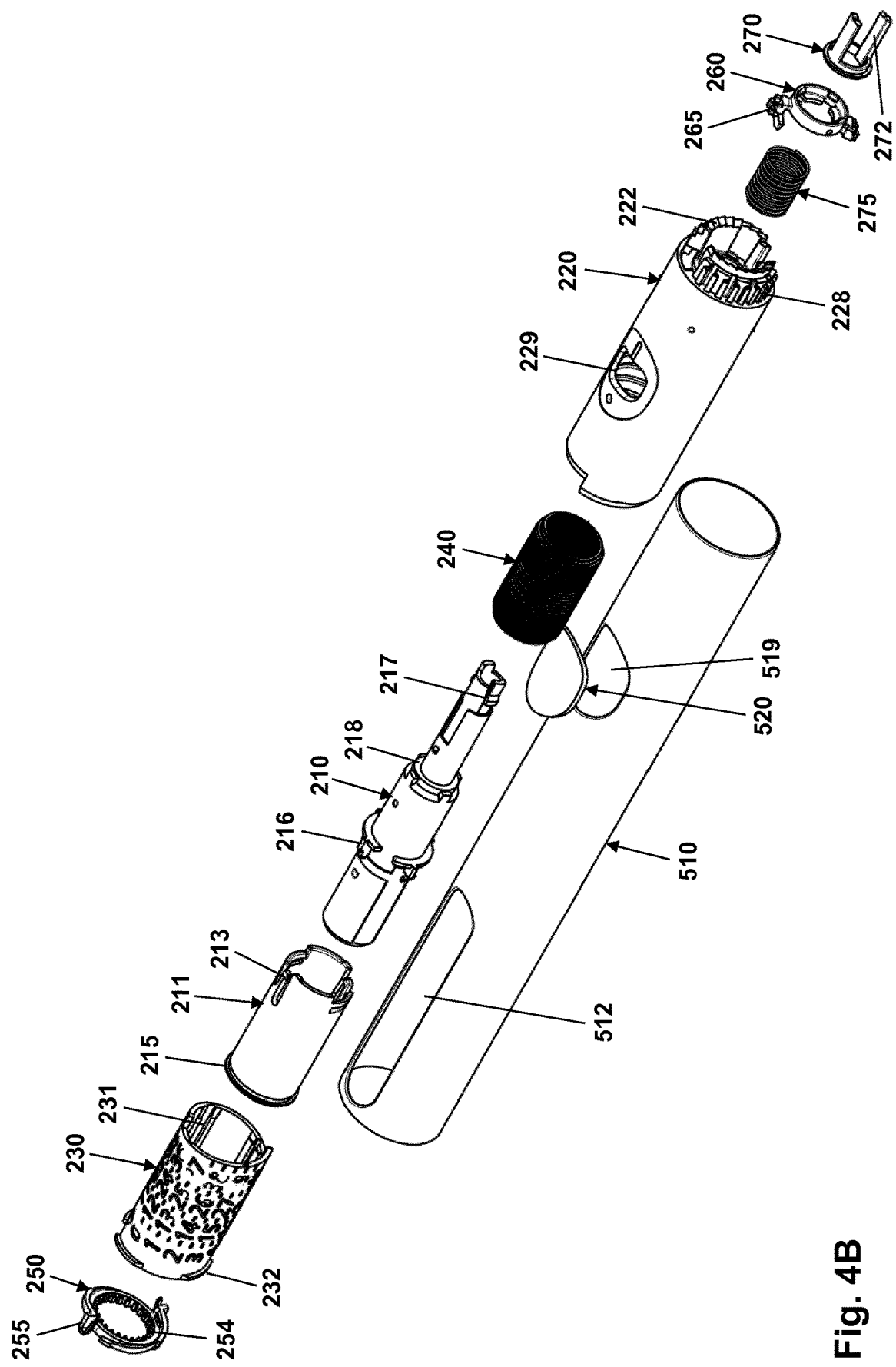
FIG. 4B shows in a rear-isometric view the second group of components of FIG. 4A.

The engine assembly 200 as shown in FIGS. 4A and 4B comprises a two-piece tubular transmission member 210, 211, a tubular engine housing member 220, a tubular scale drum 230 to be arranged between the transmission member and the engine housing member, a drive spring 240, a ring-formed clutch lock member 250, and an end-of-dose trigger assembly.

The transmission member is functionally a single member, however, in the shown embodiment it comprises a longer inner tubular member 210 and a shorter outer tubular skirt member 211 coupled to each other via coupling means 212, 213 on the inner respectively outer member, this providing a rotationally and axially locked connection, yet allows the two members to "wobble" to thereby better accommodate tolerances in the assembled pen device.

The engine housing member 220 comprises an inner helical thread 221 adapted to engage the scale drum thread structures 232 (see below), and a lateral window opening 229 allowing a user to observe numerals printed on the scale drum. At the proximal end the engine housing member comprises a reduced-diameter extension with a proximally-facing surface on which an circumferential array of ratchet teeth structures 222 there by way of example, 24 teeth) is arranged around the central opening, each tooth having a triangular configuration with an inclined ratchet surface and a stop surface oriented perpendicularly to the housing member cross-sectional plane, the ratchet teeth being configured to interface with the corresponding ratchet teeth on the ratchet member 160 (see above) to thereby provide a one-way ratchet. The reduced-diameter extension has an outer circumferential surface with a plurality of longitudinally arranged splines 228 adapted to interface with the dose setting member splines 128. The reduced-diameter extension further comprises a pair of opposed guide slot structures 225 adapted to receive the end-of-dose control member (see below). Corresponding generally to the reduced-diameter extension a tubular inner housing portion extends distally into the housing, the inner housing portion comprising at the distal end an inner circumferential flange which serves as both an axial stop surface for the transmission member stop surface 218 and as a support for the trigger spring 275 (see below).

The engine housing member 220 comprises an inner helical thread 221 adapted to engage the scale drum thread structures 232 (see below), and a lateral window opening 229 allowing a user to observe numerals printed on the scale drum. At the proximal end the engine housing member comprises a reduced-diameter extension with a proximally-facing surface on which an circumferential array of ratchet teeth structures 222 (here: 24) is arranged around the central opening, each tooth having a triangular configuration with an inclined ratchet surface and a stop surface oriented perpendicularly to the housing member cross-sectional plane, the ratchet teeth being configured to interface with the corresponding ratchet teeth on the ratchet member 160 (see above) to thereby provide a one-way ratchet. The reduced-diameter extension has an outer circumferential surface with a plurality of longitudinally arranged splines 228 adapted to interface with the dose setting member splines 128. The reduced-diameter extension further comprises a pair of opposed guide slot structures 225 adapted to receive the end-of-dose control member (see below). Corresponding generally to the reduced-diameter extension a tubular inner housing portion extends distally into the housing, the inner housing portion comprising at the distal end an inner circumferential flange which serves as both an axial stop surface for the transmission member stop surface 218 and as a support for the trigger spring 275 (see below).

The scale drum 230 is arranged in the circumferential space between the transmission member 210 and the engine housing member 220, the scale drum being rotationally locked to the transmission member via longitudinal splines 231 and being in rotational threaded engagement with the inner helical thread 221 of the engine housing member via cooperating thread structures 232, whereby the helical row of numerals passes window opening 229 in the engine housing member 220 when the drum is rotated relative to the housing by the transmission member 210. The proximal end of the scale drum comprises a stop surface 234 adapted to engage a corresponding stop surface in the engine housing member 220 to thereby provide a rotational stop for an initial (or end) rotational position, and the distal end of the scale drum comprises a further stop surface 233 adapted to engage a corresponding stop surface on the engine housing member inner surface when the maximum dose has been reached during dose setting, e.g. 100 units of insulin (IU). The stop surface 234 also serves to release the end-of-dose trigger control member 260 (see below).

The drive spring 240 is in the form of a helical open wound torsion spring with a distal hook portion (see FIG. 10A) for attachment to the transmission member and a proximal hook portion for attachment to the engine housing member. In an assembled state the drive spring is prewound to provide a desirable initial torque. In the shown embodiment the spring is formed from a rectangular wire with the longer dimension arranged corresponding to the transversal plane. The wire in a torsion spring wound from a wire having a rectangular cross section will have a tendency to tilt (rotate) under load when strained, this being the more pronounced the higher the aspect ratio of the cross section is (height divided with thickness). When the rectangular wire is tilting, the geometry will get an angular displacement relative to the springs centre axis and thus the second moment of inertia will be reduced. The stiffness of the spring will progressively drop along with the reduced second moment of inertia while the spring is being loaded, this resulting in a non-linear spring characteristic with a decaying slope. At some point, when the decreasing stiffness and the increasing load have the same magnitude, the torque of the spring will be approximately constant relative to the angular deflection of the spring. These aspects for a spring formed from a rectangular wire are described in greater detail below.

Figure 10A:
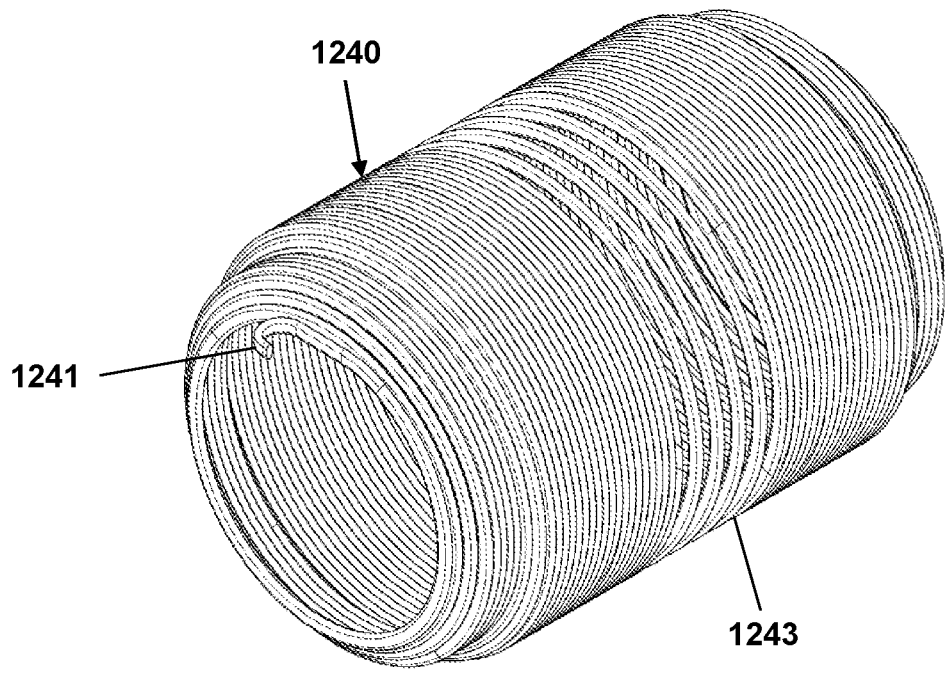
FIG. 10A shows in a front-isometric view a helical spring of the type shown in FIG. 6A.
Figure 10B:
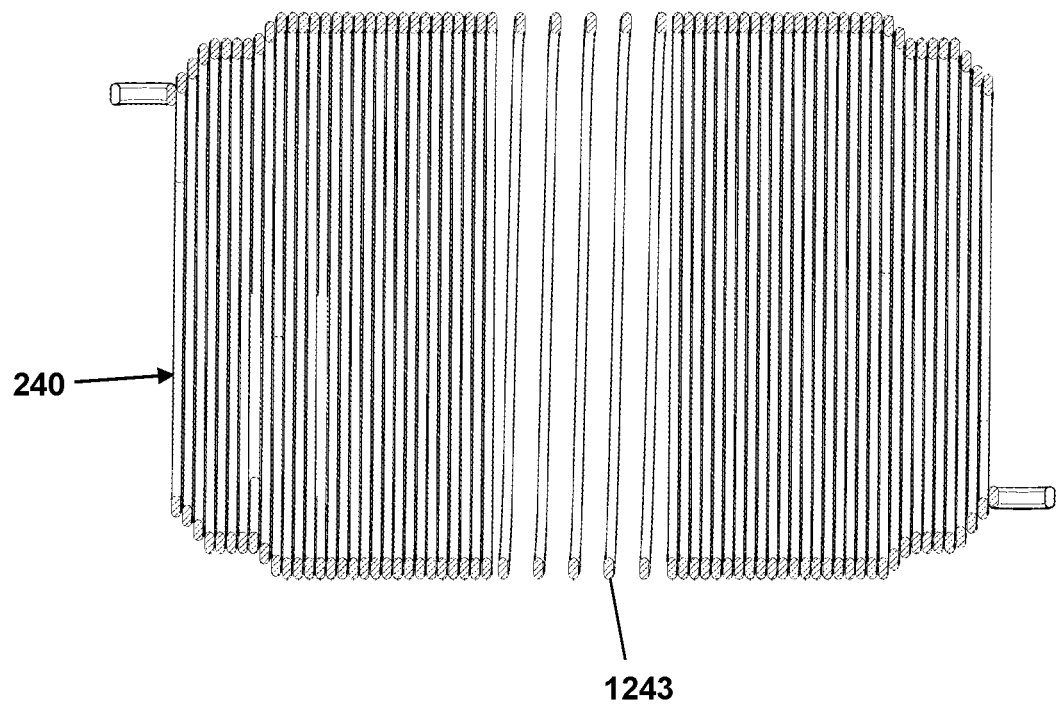
FIG. 10B shows in cross section the helical spring of FIG. 10A, FIGS. 11A-11C show screenshots for a computerized finite element analysis of a helical coil wound from a wire with a rectangular cross-section.

By utilizing this tendency, a drive spring can be designed to deliver an approximately constant torque to the piston rod in order achieve an approximately constant dosing force, this in contrast to a typical torsion spring wound from a wire with a circular cross section, in which the torque is progressing proportional with the deflection of the spring such that the force under load of the spring will be higher than the force at the initial pre-load state. An alternative configuration of the torsion spring 240 is shown in FIGS. 10A and 10B and described below. The properties of a torsion spring wound from rectangular wire is described in greater detail below with reference to FIGS. 11-14.

The ring-formed clutch lock member 250 comprises an inner surface provided with a plurality of longitudinally arranged splines 254 adapted to slidingly engage corresponding outer splines 444 on the clutch member 440 (see below), and a pair of opposed locking projections 255 adapted to non-rotationally but axially free engage corresponding grooves 475 in the drive housing (see below). Each locking projection 255 is provided with a flexible arm allowing the projection to be received in the corresponding groove 475 without play. The clutch lock member comprises (snap) coupling means allowing it to be mounted axially locked but rotationally free to the outer circumferential flange 215 of the transmission member.

The end-of-dose trigger assembly comprises a ring-formed control member 260, a trigger member 270 and a trigger spring 275. The control member 260 comprises a pair of opposed laterally projecting control arms 261 adapted to engage the engine housing member guide slot structures 225, the control arms each comprising a number of proximally facing teeth 265 adapted to engage the distally facing teeth array 125 on the skirt member 120. The trigger member 270 comprises a distal ring portion 271 and a pair of opposed proximal trigger arms 272, the ring portion being adapted to be (snap) connected to the trigger member, the connection allowing the trigger member to rotate. The two trigger arms are guided in the transmission member guiding grooves 219 and are adapted to be moved proximally through a pair of corresponding openings in the carrier member 150 when actuated. The trigger spring 275 is arranged in the tubular inner housing portion of the engine housing member 220, distally engaging the inner circumferential flange and proximally engaging the trigger control member 260.

When in an assembled state the trigger control member 260, the engine housing member guide slots 225 and the skirt member teeth array 125 interact in such a way that when the scale drum is rotated away from its zero initial position the trigger control member can be "parked" in an energized distal position when the dose button 110 is moved distally against the biasing force of the trigger spring 275 which then via the trigger control member 260 also serves as a secondary dose button return spring, the parked control member being released and moved proximally when the scale drum returns to its initial zero position, this causing the trigger member to move proximally and to thereby actuate the end-of-dose switch. At the same time an end-of-dose "click" is generated when the proximal end of the trigger arms 272 forcefully engages the housing member (with the switch interposed). The trigger arrangement is described in greater detail in EP 2016/065807.

Figure 5A:
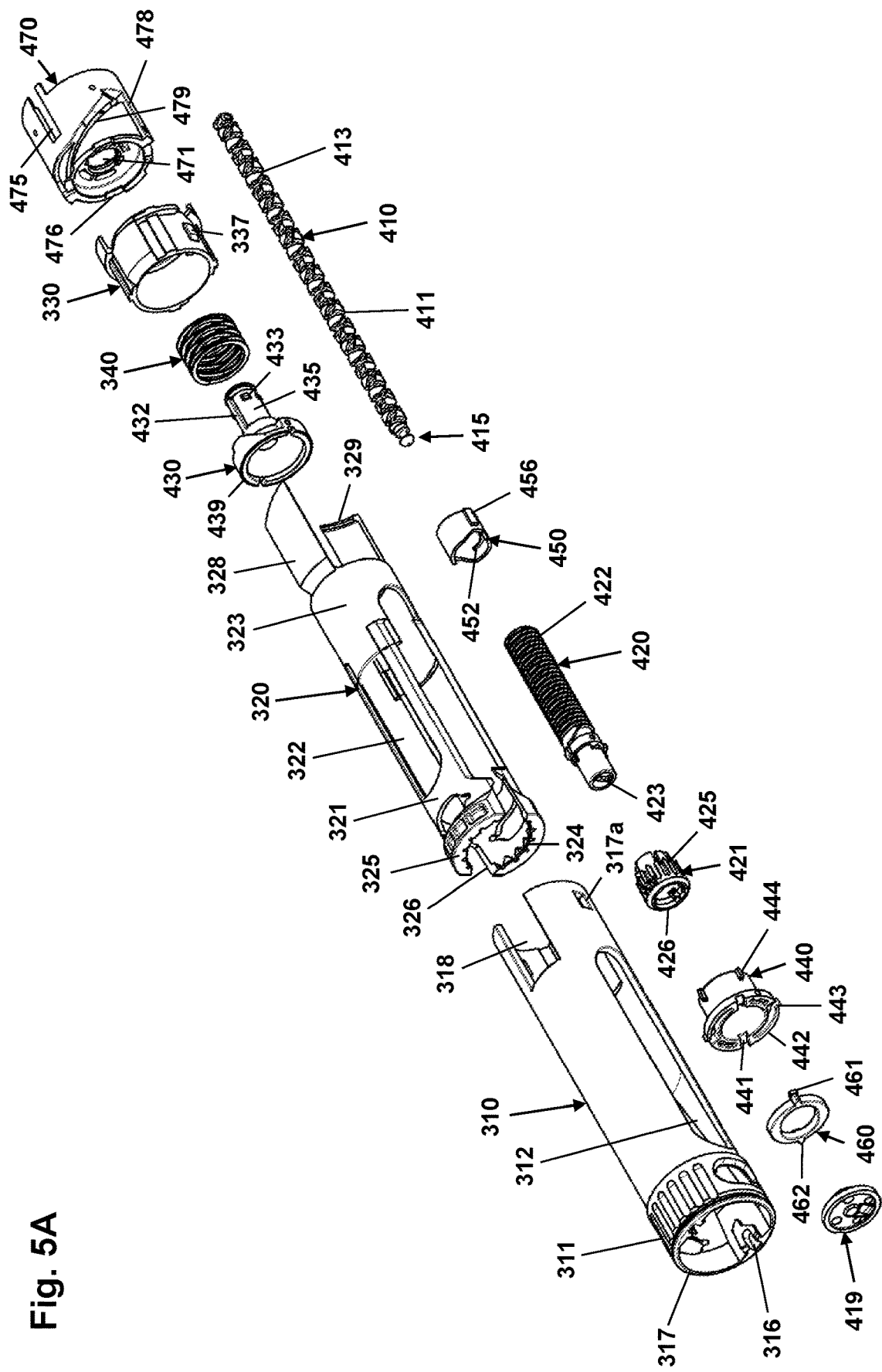
FIG. 5A shows in a front-isometric view a third group of components of the device of FIG. 2.
Figure 5B:
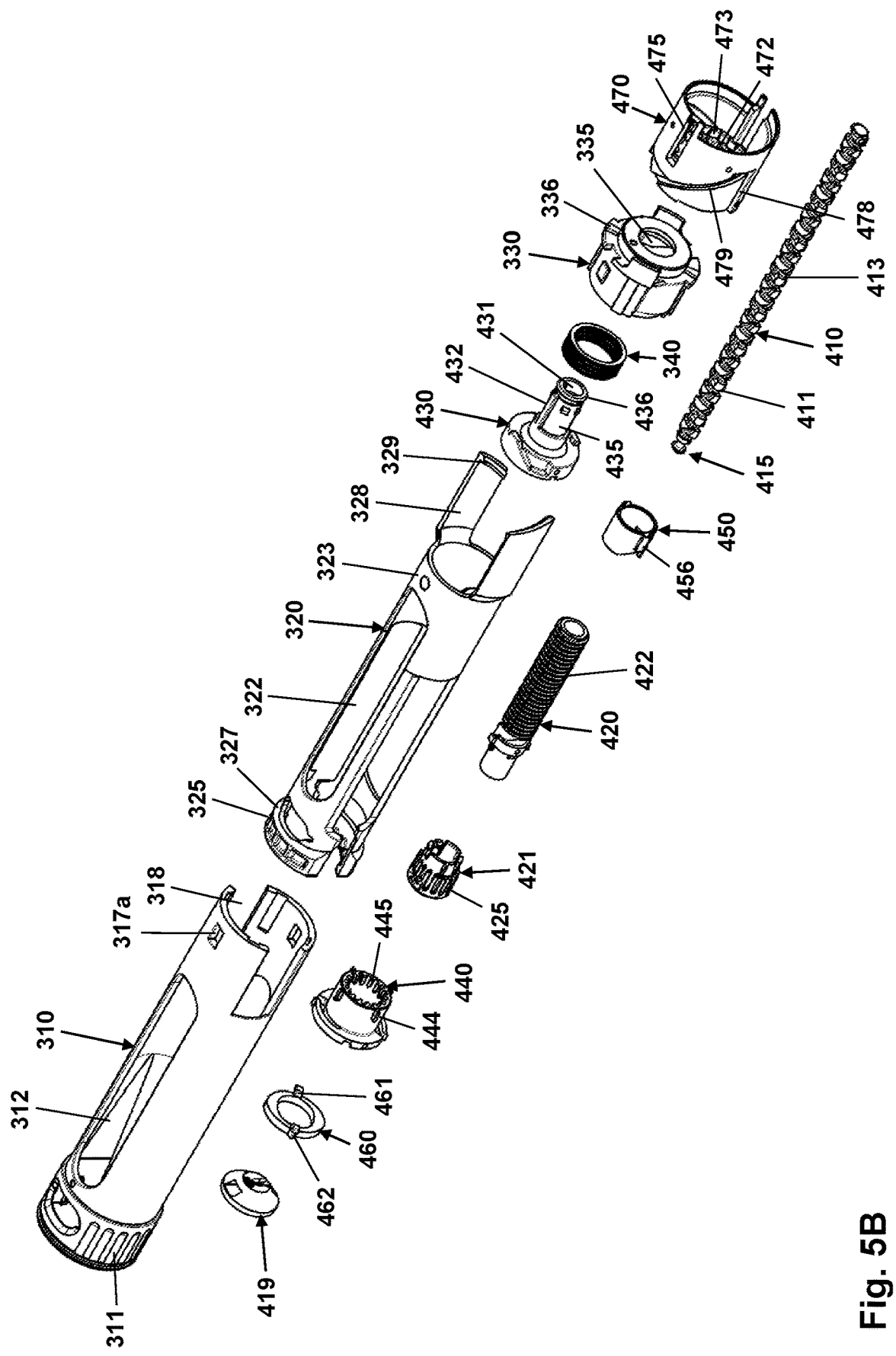
FIG. 5B shows in a rear-isometric view the third group of components of FIG. 5A.

The cartridge holder and drive assembly 300 as shown in FIGS. 5A and 5B comprises the cartridge holder sub-assembly and the drive sub-assembly 400 which are structurally integrated via the distal housing member 470 which serves as a "platform" for both assemblies. The cartridge holder is adapted to receive and hold a cartridge, the cartridge holder being actuatable between a receiving state in which a cartridge can be inserted and received in a proximal direction through a distal opening, and a holding state in which an inserted cartridge is held in an operational position, thereby providing a front-loaded cartridge holder assembly. When a cartridge has been inserted and the cartridge holder has been closed, the components of the driver sub-assembly serves to translate the rotational movement of the released transmission member into axial movement of the piston rod in the distal direction. When the cartridge holder is opened it also releases (in an assembled pen) the drive sub-assembly allowing the piston rod to be returned to a proximal position.

The drive sub-assembly comprises a double-threaded piston rod 410 in a first threaded engagement with a two-piece tubular drive member 420 and a second threaded engagement with a tubular nut member 430. The driver sub-assembly further comprises a tubular clutch member 440, an end-of-content member 450 arranged in threaded engagement on the drive member, a ring-formed brake member 460 as well as the above-mentioned distal housing member 470.

The drive member 420 is functionally a single member, however, in the shown embodiment it comprises for moulding and mounting purposes a main tubular member 420 and a distal shorter outer tubular member 421 fixedly coupled to each other via e.g. snap coupling means. The (combined) drive member comprises an outer threaded portion 422 adapted to engage a corresponding inner thread 452 on the end-of-content member 450, an inner thread 423 adapted to engage the corresponding "drive thread" on the piston rod, and on the distal portion an array of outer splines 425 adapted to slidingly engage corresponding inner splines 445 on the clutch member 440. The distal end further comprises circumferential (snap) connection means 426 allowing the drive member to be connected to the proximal flange 436 of the nut member 430 (see below).

The tubular clutch member 440 comprises a tubular portion having a proximal inner spline array 445 adapted to slidingly engage the corresponding outer splines 425 on the drive member 420, 421, and a proximal outer spline array 444 adapted to slidingly engage the corresponding inner splines 214 on the transmission member 210, 211 as well as the inner splines 254 on the clutch lock member 250. In this way the clutch member serves as a platform for engaging and disengaging the different members and thereby controlling rotational movement of these members. The clutch member 440 further comprises a distal circumferential flange having a distal surface with a pair of opposed guide grooves 441 for guide projections 461 on the brake element 460. Circumferentially on the flange a pair of opposed circumferentially extending flexible ratchet arms 442 are provided each having a ratchet tooth 443 at the free end adapted to engage a corresponding circumferential array of ratchet teeth on the distal housing member 470, this providing a one-way ratchet mechanism which produces a clicking sound during out-dosing.

The tubular end-of-content member 450 comprises an inner thread 452 adapted to engage the outer threaded portion 422 on the drive member 410, and a pair of opposed longitudinal drive flanges 456 adapted to engage the inner drive slots 216E on the transmission member 210.

The ring-formed brake element 460 has a pair of opposed laterally extending guide projections 461 each having a proximally facing surface adapted to slidingly engage the guide grooves 441 in the clutch member 440, as well as a laterally facing pointed tooth structure 442 adapted to engage a circumferential serrated brake surface arranged on the inner surface of the distal housing member 470, this providing that the brake element is moved back and forth in the guide grooves when the clutch member rotates relative to the distal housing member, this providing a braking effect. Such a brake arrangement is described in greater detail in WO 2015/055642.

The distal housing member 470 comprises a tubular portion with an inner distal flange portion having a central opening 471 for receiving and axially guiding the nut member 430. The inner tubular surface comprises a circumferential array of ratchet teeth 473 adapted to engage the ratchet teeth 443 on the clutch member as well as a circumferential serrated brake surface 472 adapted to engage the teeth structures 462 on the brake member. The clutch member 440 is mounted axially locked in the distal housing member 470 by means of a pair of opposed snap protrusions 474 (see FIG. 8A) allowing the flexible ratchet arms 442 to snap axially in place distally of the snap protrusions 474 during assembly. As will be described in greater detail below the distal housing member further comprises a number of control structures on the outer tubular surface adapted to cooperate with corresponding structures of the cartridge holder assembly.

The tubular nut member 430 comprises a distal cup-shaped portion and a reduced-diameter proximal tubular portion 435. The tubular portion comprises an inner "propulsion thread" 431 adapted to engage the corresponding propulsion thread 411 on the piston rod 410. On the outer surface the tubular portion 435 comprises a pair of opposed longitudinal flanges 432 adapted to be axially received and guided in the central opening 471 of the distal housing member, a number of stop projections 433 preventing that the nut member can be moved distally out of engagement with the distal housing member 470, as well as a circumferential proximal (snap) flange 436 adapted to engage the circumferential (snap) connection means 426 on the drive member allowing the two members to rotate relative to each other. The proximal surface of the cup-shaped portion is adapted to engage a spring (or spring assembly) of the cartridge holder assembly (see below), and the distal circumferential edge 439 of the cup portion is adapted to engage the rear circumferential edge of a loaded cartridge.

The double-threaded piston rod 410 comprises a first "drive thread" 413 adapted to engage the drive thread 423 on the drive member 420 and a second "propulsion thread" 411 adapted to engage the propulsion thread 431 in the nut member 430, the two threads being imposed on each other along the length of the piston rod. The purpose of the drive thread is to rotate the piston rod as the drive member 420 rotates, whereas the purpose of the propulsion thread is to move the piston rod axially through the (during out-dosing) stationary nut member 430. In most traditional drug delivery devices having a piston rod which is rotated by a driver during out-dosing, the "drive thread" is in the form of one or more axially oriented grooves, this providing that the driver and piston rod rotate together 1:1. By giving the drive thread an inclination a gearing is provided, e.g. 2:1 meaning the driver will rotate twice to rotate the piston rod a full rotation. At the distal end the piston rod comprises a coupling structure 415 for a piston washer 419, e.g. providing a ball-and-socket snap coupling.

In an assembled and operational state the drive sub-assembly engages the transmission member 210, 211 which via the clutch member 440 rotates the drive member 420 and thereby the piston rod 410 which is then moved axially in the distal direction through the nut member 430.

The cartridge holder sub-assembly 300 comprises a user operated generally tubular actuation sleeve 310 adapted to receive a generally tubular cartridge holder 320, a tubular base member 330, a spring assembly 340 and the above-described distal housing member 470. The cartridge holder is adapted to receive and hold a generally cylindrical drug-filled cartridge 20 (see FIG. 6A) comprising a needle hub mount with a circumferential flange with a number of distally facing pointed projections serving as a coupling means for the cartridge holder assembly as will be described in more detail below. A hub mount of the shown type is described in U.S. Pat. No. 5,693,027.

The cartridge holder 320 comprises a pair of opposed flexible arms 321 extending distally from a ring portion 323, each arm being provided with a distal gripping portion, or "jaw", 325 having a plurality of proximal facing gripping teeth 324 spaced circumferentially to engage the above-described distally facing pointed projections on the cartridge. Between the jaws a distal opening is formed adapted to receive a cartridge when the cartridge holder assembly is in the receiving state. Two opposed oblong openings (or windows) 322 are formed in the cartridge holder, one in each arm, each window being aligned with a corresponding oblong window 312 formed in the tubular actuation sleeve, the two pairs of windows moving together in rotational alignment. Each gripping portion 325 comprises an outer proximally-facing inclined and curved surface 327 adapted to engage a correspondingly curved distal circumferential edge 317 of the sleeve member 310, as well as a pair of inclined distally-facing actuation surfaces 326 adapted to engage a pair of corresponding inclined proximally facing actuation surfaces 316 arranged on the inner surface of the actuation sleeve 310. The cartridge holder further comprises a pair of opposed circumferentially curved drive arms 328 extending proximally from the ring portion 323, each arm comprising an inclined proximal edge with an inner gripping flange 329 adapted to engage a corresponding control track 479 on the distal housing member 470. It should be noted that in FIG. 5A the cartridge holder 320 comprises an alternative configuration for the purpose of displaying certain features in that the drive arms 328 have been offset 90 degrees relative to the remaining cartridge holder just as the cartridge holder as a whole has been offset 90 degrees relative to the actuation sleeve 310. In FIG. 5B the cartridge holder 320 is depicted correctly.

The tubular actuation sleeve 310 comprises a distal circumferential gripping portion 311 allowing a user to grip and rotate the actuation sleeve, the gripping portion being provided with the above-described circumferential edge 317 and actuation surfaces 316 as well as a pair of opposed openings 317a allowing a user to observe the neck portion of a mounted cartridge. Two opposed windows 322 are formed in the actuation sleeve, each window being aligned with the corresponding window 312 formed in the cartridge holder 310. The proximal portion of the actuation sleeve comprises a pair of opposed openings 317a serving as snap coupling means for the base member (see below), as well as a pair of opposed guide slots 318 adapted to slidingly and non-rotationally receive the cartridge holder drive arms 328, thereby providing that the two members rotate together.

The cup-formed base member 330 comprises a tubular distal portion adapted to accommodate the nut member 430 and the spring assembly 340, the tubular portion comprising on the outer surface a pair of opposed protrusions 337 adapted to fixedly snap-engage the openings 317 in the actuation sleeve. The base member comprises a proximal circumferential inner flange with a central opening 335 adapted to receive the proximal tubular portion 435 of the nut member 430. The base member further comprises on the proximal peripheral portion a number of locking projections 336 adapted to rotationally and slidingly engage corresponding cut-outs 476 in the distal housing member 470 to thereby provide a rotational lock. In the shown embodiment four projections are provided with an off-set of 90 degrees corresponding to a full rotational actuation of the actuation sleeve. As the base member 330 and the distal housing member 470 are biased into engagement by the spring assembly 340, the projections will serve as a rotational lock when the projections are moved in and out of engagement during rotation.

The spring assembly 340 comprises a number of stacked disc springs but could also be in the form of a single helical spring. The spring assembly is arranged in the base member 330 cup portion and provides a distally directed biasing force on the cup portion of the nut member 430.

The distal housing member 470 comprises an opposed pair of part-helical guide tracks 479 on the exterior surface adapted to engage the gripping flanges 329 on the cartridge holder drive arms 328, this providing that the cartridge holder is moved axially back and forth when the actuation sleeve 310 is rotated back and forth between an open and a closed state. The distal housing member further comprises rotational stop surfaces 478 adapted to engage corresponding stop surfaces on the cartridge holder drive arms 328 and/or the actuation sleeve 310.

In an assembled state the gripping jaws 325 are moved in and out as the user rotates the actuation sleeve between its two rotational stops, the axial movement being controlled by the guide tracks 479 as described above. More specifically, the inclined actuation surfaces 316 will force the gripping jaws outwardly to their open position as the actuation surfaces 326 are moved distally and into sliding contact with the sleeve actuation surfaces 316. Correspondingly, when the arms are moved proximally the outer curved surfaces 327 engage the actuation edges 317 on the actuation sleeve and are thereby forced inwardly into their gripping position. However, when a new cartridge is inserted it is necessary to move the piston rod proximally. For this purpose the integrated cartridge holder and drive assembly provides that the drive sub-assembly is operated between a loading state in which the piston rod can be moved proximally and a dosing state in which the piston rod cannot be moved proximally but only rotated distally.

More specifically, when the cartridge holder is opened the cartridge no longer exerts a proximally directed force on the nut member edge 439, the nut member 430 and thereby the thereto attached drive member 420, 421 is moved distally by the spring assembly 340, the drive member outer splines 425 thereby disengaging the inner splines 445 on the clutch member 440, this allowing the drive member 410, 421 and thereby the piston rod 410 to rotate and thereby the piston rod to be moved proximally. At the same time the rotating drive member provides that the end-of-content member 450 is moved proximally, e.g. to its initial proximal-most position when a fully filled cartridge is loaded. When the cartridge distal edge engages the nut member 430 the nut member and the piston rod will move proximally together, this essentially eliminating air gap between the piston rod and the cartridge piston. When the user during insertion of a new cartridge starts feeling the resistance from the spring assembly 340 most users will rotate the actuation sleeve to close the cartridge holder thereby operate the gripping arm portions 325 to move the cartridge to its proximal operational position. At the same time the drive member outer splines 425 re-engages the inner splines 445 on the clutch member 440, thereby rotationally locking the drive member 420, 421 and thus the piston rod. In this state rotation of the drive member is via the clutch member 440 prevented by the rotationally locked clutch lock member 250.

In case the drug delivery device with a mounted drug cartridge is being stored under low temperatures allowing the fluid drug formulation to freeze and thus expand, the expansion will result in oppositely directed forces exerted on the nut member 430 respectively the gripping arm portions 325 and thereby the entire cartridge holder 320. Due to the helical engagement with the guide tracks 479 the distally-directed force on the cartridge holder will result in a rotational force which for a given threshold will result in the rotational force overcoming the locking force of the rotation lock 336, 476 which then will result in the cartridge holder "pop open", this protecting the pen mechanism for mechanical damage.

The outer housing assembly 500 as shown in FIGS. 4A and 4B comprises an essentially tubular housing member 510 and a transparent window member 520. Two opposed oblong windows 512 are formed in the distal portion, the corresponding oblong windows 312 formed in the tubular actuation sleeve being rotationally aligned therewith when the actuation sleeve is in its closed position. The housing member 510 further comprises a window opening 519 adapted to receive the window member 520, the corresponding window opening 229 in the engine housing member 220 being axially and rotationally aligned therewith when the device is being assembled, the outer window opening 519, and thus the window member 520, being larger than the inner window opening 229. The outer housing may be formed from e.g. metal or plastic and serves when mounted to both protect and stabilize the device, e.g. by holding the drive arm gripping flanges 329 engaged in the control tracks 479 on the distal housing member 470, and by preventing bending between the cartridge holder portion and the inner housing corresponding to the rotational interface there between. In the shown embodiment the distal gripping portion 311 and the transparent window member 520 are designed to be essentially flush with the outer surface of the housing member in an assembled state.

The cap assembly 600 as shown in FIGS. 3A and 3B comprises a tubular cap housing member 610, a clip member 620 and an inner cap member 630, the cap housing member inner diameter being dimensioned to snugly receive the outer housing member 500. The cap housing member 610 comprises at the distal end a cut-out 611 adapted to receive a clip base portion, as well as a (snap) opening 612 adapted to engage the skirt member 630. The clip member 620 comprises a generally tubular skirt portion 622 with a closed distal end, the skirt portion comprising a clip base 621 from which a flexible clip portion 623 extends in a proximal direction, as well as a number of (snap) structures 624 adapted to engage corresponding (snap) coupling structures on the inner cap member 630. The inner cap member 630 has a generally tubular configuration with a proximally extending flexible arm 632 with a proximal gripping edge 631 adapted to releasably engage the distal gripping portion 311 when the cap is mounted, the flexible arm also being adapted to snap into engagement with the cap housing member opening 612. The inner cap member further comprises a number of (snap) structures 634 adapted to engage corresponding (snap) structures 624 on the clip member. During assembly the inner cap member 630 is inserted in the cap housing member 610 and snaps in place, the clip member 620 being inserted into the inner cap member 630 snapping into engagement.

During final assembly of the cartridge holder and drive assembly 300 is first attached to the engine assembly 200. More specifically, the proximally protruding piston rod 410 and drive member 420 with the mounted end-of-content member 450 are inserted into the transmission member, the end-of-content member drive flanges 456 thereby engaging the inner drive slots 216E on the transmission member 210. During this operation it is to be assured that the piston rod and the end-of-content member are positioned axially corresponding to the initial zero state of the device. The two assemblies are held together when the engine housing member 220 and the distal housing member 470 are connected to each other by e.g. welding which allows axial tolerances to be compensated. Next the outer housing member 510 is slid onto the engine housing member from the proximal end such that housing window opening 511 is aligned with window opening 229 in the engine housing member 220, where after the transparent window member 520 is mounted in the outer housing window opening and in engagement with the engine housing outer surface surrounding the window opening 229. Subsequently the window member 520 is secured to the engine housing member 220 by e.g. welding or adhesive, this axially and rotationally securing the outer housing member to the inner housing. At this point the proximal end of the transmission tube 210 extends slightly out of the housing. Finally the dose setting and logging assembly 100 is inserted into the proximal end of the pen outer housing causing the carrier member connector tube portion 153 to snap engage the proximal transmission tube coupling means 217, thereby rotationally and axially securing the dose setting and logging assembly 100 to the rest of the pen device. As a finishing touch the cap 600 is mounted.

Figure 6B:
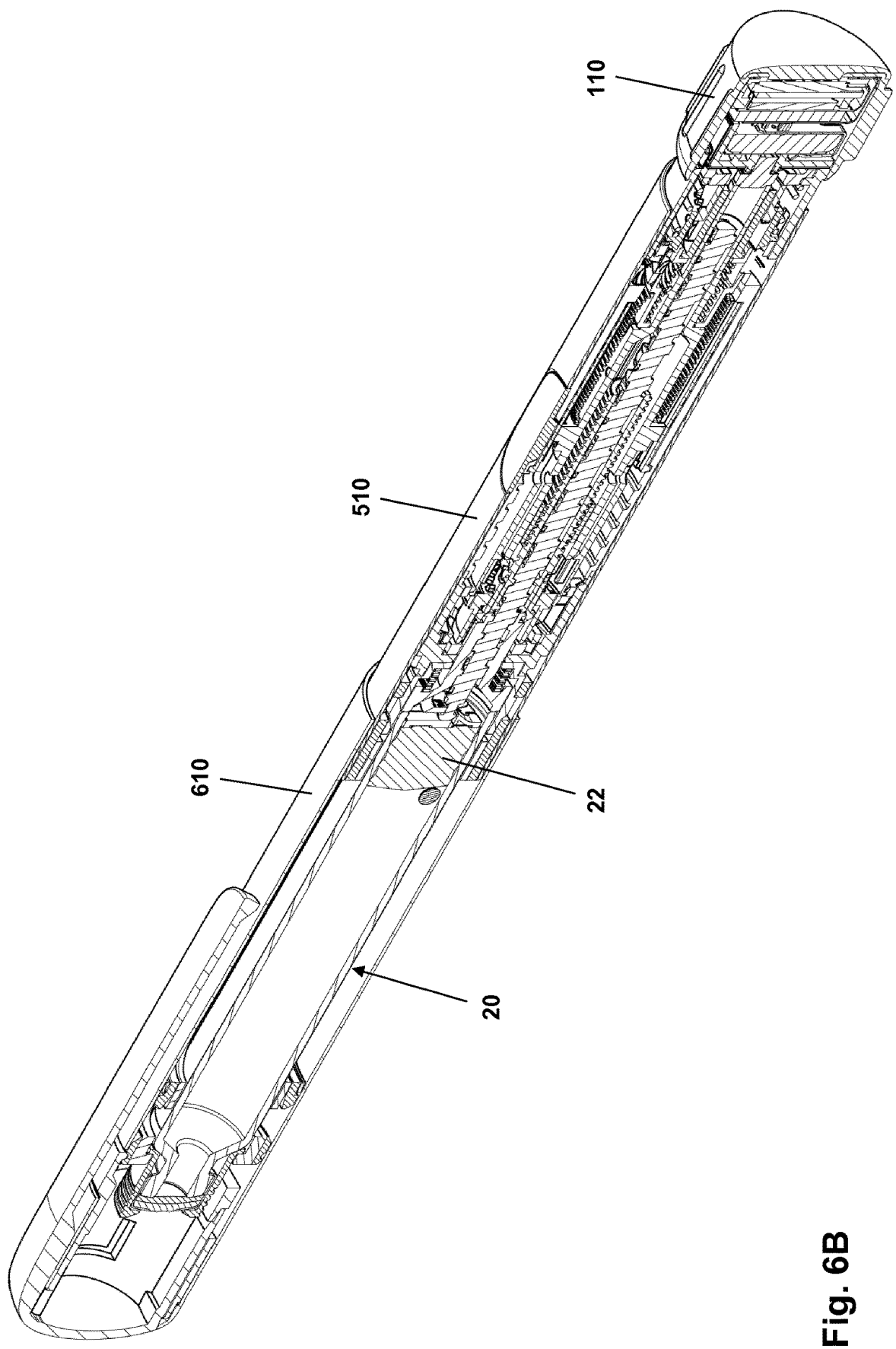
FIG. 6B shows in a cross-sectional rear-isometric view the device of FIG. 1.
Figure 7A:
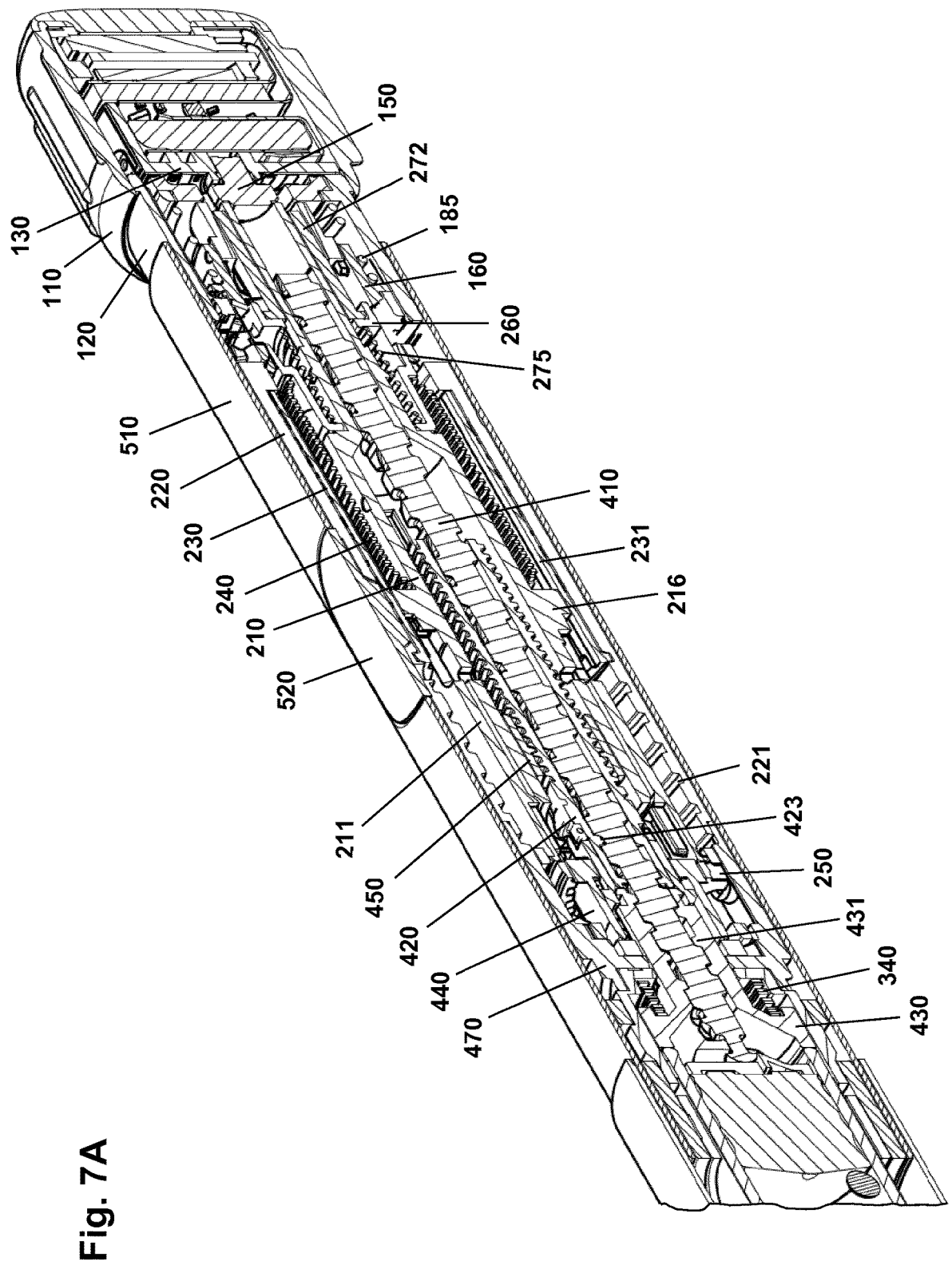
FIG. 7A shows a proximal portion of the device as shown in FIG. 6A.
Figure 7B:
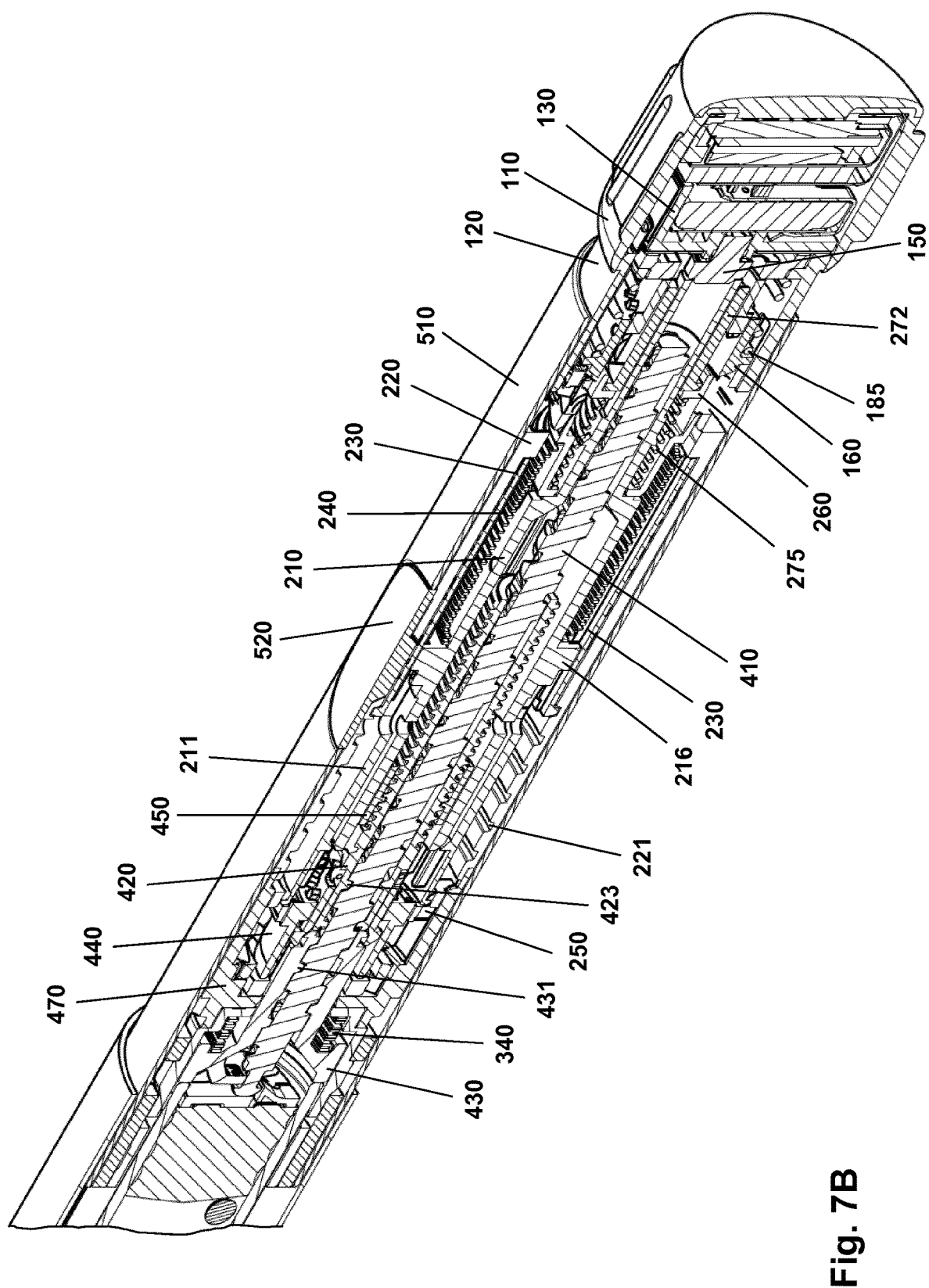
FIG. 7B shows a proximal portion of the device as shown in FIG. 6B.

Cross-sectional views of an assembled drug delivery device as described above is shown in FIGS. 6A and 6B. To better show the individual components and their relationship FIGS. 7A and 7B show the proximal portion of the device in cross-sectional views.

In operation when setting a dose the dose setting member 110 in its proximal position is rotated clockwise, this rotating the entire dose setting and logging assembly 100 together with the transmission tube due to the carrier member 150 being non-rotationally mounted on the transmission tube. Hereby the drive spring 240 is strained and the end-of-content member 450 moved distally on the drive member 420 corresponding to the size of the set dose. As the drive surfaces of the drive-lift control member 170 are in engagement with the corresponding drive surfaces on the ratchet member 160 the latter is forced to rotate together with the dose setting member 110 to the desired rotational position, this resulting in the ratchet member ratchet teeth 162 passing over the engine housing ratchet teeth 222 during which the ratchet member 160 is moved back and forth due to the inclined ratchet teeth, the ratchet spring 185 and the splined connection 161, 191 with the release member 190. The dose can be set in increments corresponding to one ratchet tooth which e.g. for a given insulin delivery device typically will correspond to one unit (IU) of insulin formulation. When the maximum dose has been set, i.e. the scale drum max stop has engaged the engine housing max stop or the end-of-content member 450 has reached its distal stop, further rotation of the dose button will result in the drive surfaces on the drive-lift control member 170 to cam over due to the slight inclination of the cooperating drive surfaces on the control member 170 respectively the ratchet member 160, the latter being moved back and forth against the bias of the ratchet spring. During dose setting the mode switch arm 180 is positioned on the mode switch array 143 corresponding to the dose setting mode.

When decreasing a set dose the dose setting member is rotated counter-clockwise whereby the inclined lift surfaces on the drive-lift control member 170 in engagement with the corresponding lift surfaces on the ratchet member 160 moves the latter proximally against the ratchet spring until the ratchet member ratchet teeth 162 just disengages the housing member ratchet teeth 222, at which point the force from the strained drive spring 240 will rotate the transmission member 210 counter-clockwise and thereby also the ratchet member 160, this resulting in the inclined lift surfaces disengaging each other. As a consequence the ratchet member 160 can be moved distally by the ratchet spring whereby the ratchet teeth will re-engage, this corresponding to the previously set dose having been decreased by one increment. If the user continuous to rotate the dose setting member 110 counter-clockwise the set dose will continue to be reduced by one increment for each back and forth movement of the ratchet member. At the same time the end-of-content member 450 and the scale drum 230 is also rotated counter-clockwise and the dose size shown in the display window 229 is reduced correspondingly. Due to its design the ratchet mechanism has a built in protection against overload in the resetting direction. When the user tries to dial below zero the ratchet is axially deflected by the lifting teeth connected to the dial, and the ratchet disengages the one way teeth's in the housing, but as there are no drive spring force to move the ratchet in the resetting direction the ratchet will only move further axially until the lifting teeth moves to the next engagement and the ratchet returns to the initial axial position.

Figure 9A:
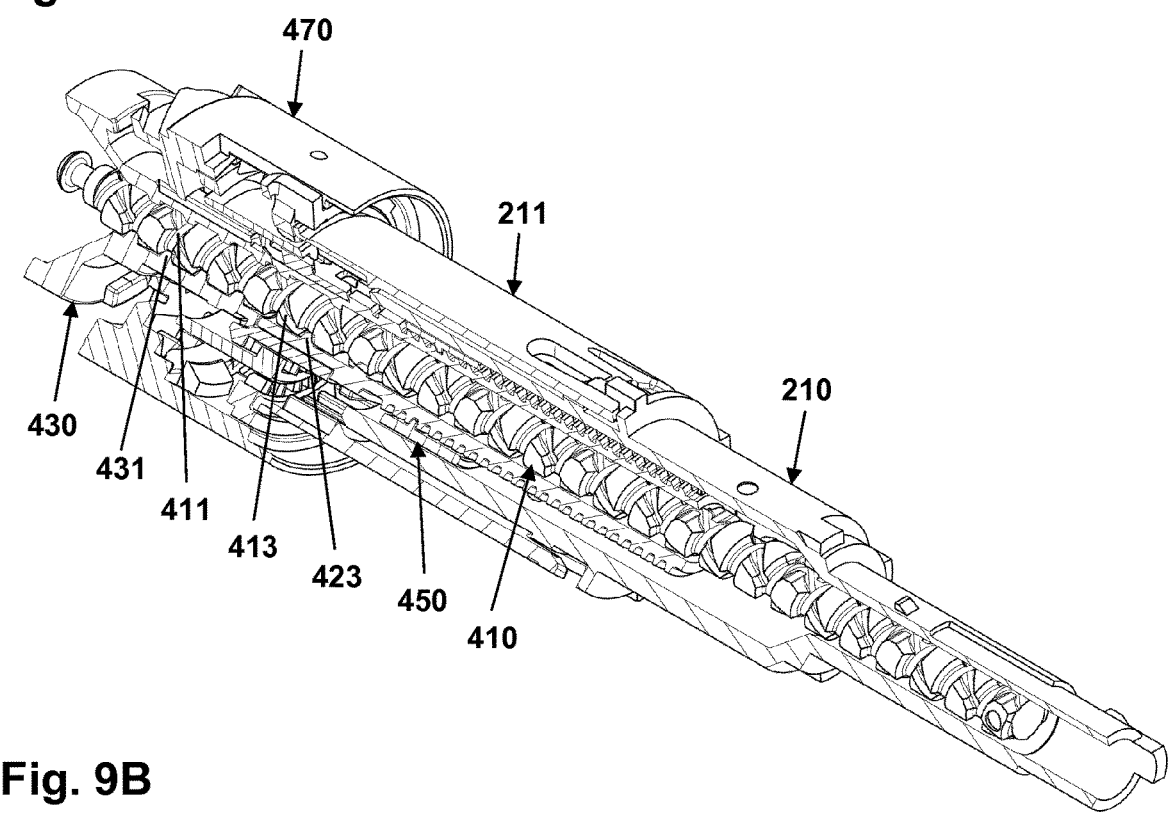
FIG. 9A shows in a second partial cut-away view a portion of the expelling mechanism in a dose setting mode.
Figure 9B:
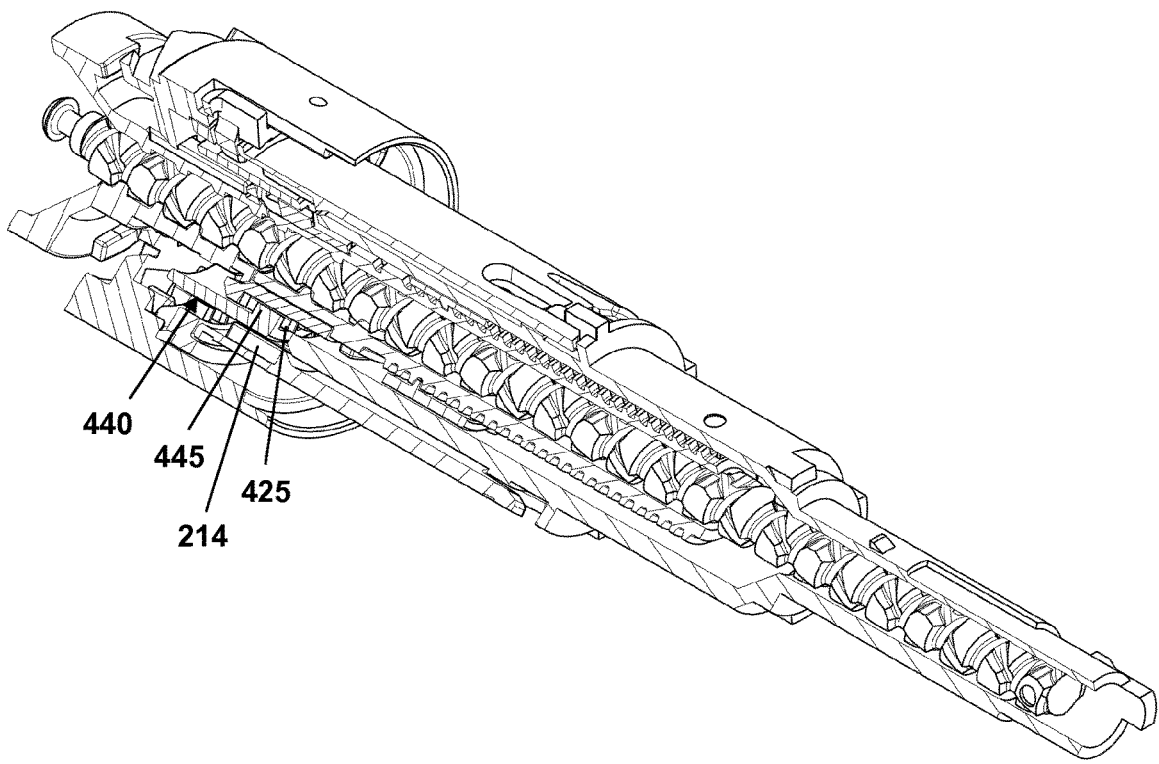
FIG. 9B shows the expelling mechanism of FIG. 9A in a dose expelling mode.

To expel a set dose of drug the combined dose setting and release button member 110 is moved distally against the biasing force of the ratchet spring 185 from a proximal-most to a distal-most position during which a series of engagements and dis-engagements between the above-described components take place. As described above, the dose button assembly 100 is axially coupled to the transmission member 210, 211. FIGS. 8A and 8B as well as FIGS. 9A and 9B show the distal coupling arrangements in the dose setting respectively the dose expelling mode.

Firstly the dose button skirt splines 128 engage the splines 228 of the engine housing to prevent further rotational adjustment of the set dose. At the same time the skirt member teeth array 125 engages the trigger member control arms teeth 265 to actuate the trigger control member.

Secondly the inner splines 214 at the distal end of the transmission member 210, 211 start to engage the clutch member outer splines 444 to lock the two members rotationally. At the same time the inner splines 254 of the clutch lock member 250, which is axially coupled to the transmission member distal flange 215, start to disengage the clutch member outer splines 444, whereby the clutch member 440 rotational lock with the engine housing via the clutch lock member 250 is released. Due to the splined engagement between the clutch member 440 and the clutch lock member 250 it is assured that the clutch member in the rotationally locked state is parked and held in an "incremental position" providing for easy engagement with the transmission member 210, 211. At this state of operation the switch array 143 has been moved into the intermediate mode as controlled by the stationary switch arm 180. FIGS. 8A and 8B as well as FIGS. 9A and 9B show the distal coupling arrangements in the dose setting respectively the dose expelling mode.

Thirdly the array of outer splines 191 on the release member 190, which is axially coupled to the dose button and transmission tube, disengages the ratchet member splines 161 thereby allowing the strained drive spring 240 to rotate the transmission tube which via the clutch member 440 rotates the drive member 420, 421, which again via the threaded drive engagement 423, 413 rotates the piston rod 410 which is hereby axially moved distally via the threaded propulsion engagement 411, 431 with the nut member 430. At the same time the scale drum 230 is rotated backwards towards its initial zero position, the currently remaining amount of drug to be expelled being displayed in the window 229. During disengagement between the release member and the transmission member, but before full disengagement has taken place, the switch array 143 has been moved into the dose expelling mode as controlled by the stationary switch arm 180.

During rotation of the clutch member 440 the brake member 460 is moved back and forth in the transversal plane due to its engagement with the distal housing 470. During normal operation only a small amount of energy is dissipated, however, if the set expelling mechanism is released without the piston rod in engagement with a cartridge piston, much more energy can be dissipated as the piston rod is moved distally without resistance, this providing an essential amount of braking which prevents damage to the mechanism.

Further, during rotation of the transmission member 210 the thereto fixedly attached carrier member 150 rotates, this rotating the contact disc 155 relative to the PCB sensor portion 142, this allowing the electronics to determine the amount of rotation during an expelling event and thereby the size of a corresponding expelled dose amount.

At the end of an expelling event the scale drum stop surface 234 engages the engine housing stop surface to thereby also stop rotation of the transmission member and thereby out-dosing. At the same time the scale drum rotates the trigger control member 260 out of its parked engagement with the engine housing, thereby allowing the trigger spring to move the trigger member arms 272 proximally to thereby actuate the end-of-dose switch. At the same time an end-of-dose "click" is generated when the proximal end of the trigger arms 272 forcefully engages the housing member 130 (with the switch interposed). In this way the logging electronics can determine that a given set dose has been fully expelled, this in contrast to a situation in which a user has paused an out-dosing event.

When a user removes the applied force from the dose button 110 the above-described clutch and switch components will engage and dis-engage in the reverse order. When an expelled dose amount has been determined and the switch array 143 returns to the dose setting mode the just expelled dose will be shown in the display 149 for a number of seconds. If no dose has been set and the dose button is actuated and subsequently released, the detected movement can be used to control the display to show e.g. the last expelled dose size and the time since then.

Returning to the torsion drive spring 240 as described above with reference to FIG. 4A an alternative configuration will be described. More specifically, FIGS. 10A and 10B shows a drive spring 1240 the form of a helical partly open wound torsion spring with a distal hook portion 1241 for attachment to the transmission member and a proximal hook portion for attachment to the engine housing member. The spring comprises proximal and distal portions with the coils wound in contact with each other, i.e. a closed configuration, as well as a central portion 1243 in which the spring has an open configuration with the individual coils wound with an axial distance there between. In the cross-sectional view of FIG. 10B the rectangular cross section 1243 of the spring wire can be seen. In the shown embodiment the height dimension of the wire is larger than the thickness dimension. By this arrangement the closed portions provide an axially compact spring design whereas at the open portion provides an axial flexibility allowing the spring to be compressed axially during mounting and operation.

In the field of springs wound from rectangular wire, the wire is said to be wound "on flat" when the larger of the two dimensions of the rectangle faces the spring axis, respectively "on edge" when the smaller of the two dimensions of the rectangle faces the spring axis. As appears and as illustrated in FIG. 10B the herein described specific embodiments of a drive spring are wound with the rectangular wire on "edge", i.e. with the height h being larger than the thickness t as shown in FIG. 13.

Figure 13:
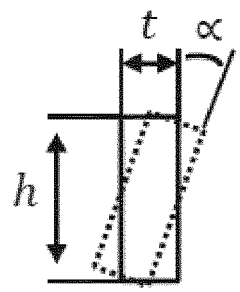
FIG. 13 shows the parameters for calculation of the second moment of inertia for a spring wire.

For a given cross-section of a spring the rectangular wire may have an ideal non-tilted orientation with the shorter side of the rectangle oriented in parallel with spring axis, a tilt angle α being defined as a deviation from this non-tilted orientation, i.e. relative to a normal to the spring axis as shown in FIG. 13.

Whereas in a mathematical model for a spring a perfect rectangle normally is used, a "real" spring will in most cases deviate from such a model, e.g. by having rounded edges and opposed surfaces being not perfectly in parallel. In respect of the latter it should be noted that when a square or rectangular wire is coiled, the wire cross-section deforms slightly into a keystone or trapezoidal shape, i.e. the wire is stretched and thus "thinned" corresponding to the outside portion of the wire. This issue can be addressed by utilizing a "keystoned" wire which has been processed especially so that deformation during spring winding or coiling causes the cross section to become approximately rectangular. Thus, the context of the present application, "rectangular" thus broadly covers any "rectangular-like" wire cross sectional form which can be inscribed in a given rectangle having the dimensions h and t, h being larger than t, e.g. an oval or trapezoidal cross section.

As described above with reference to FIG. 3A the rectangular cross section of the coil wire may be used to provide a torsion spring with a non-linear spring characteristic having a decaying slope. The characteristics of such a spring will be described in greater detail with reference to FIGS. 11-14.

Figure 11A:
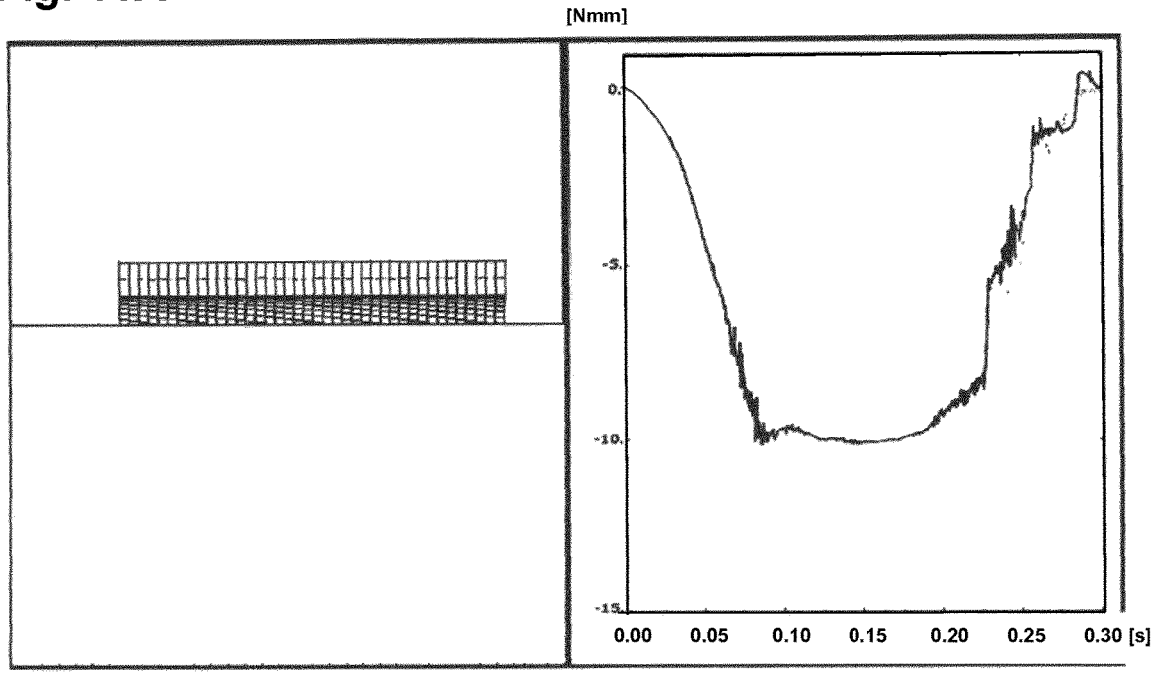
Figure 11B:
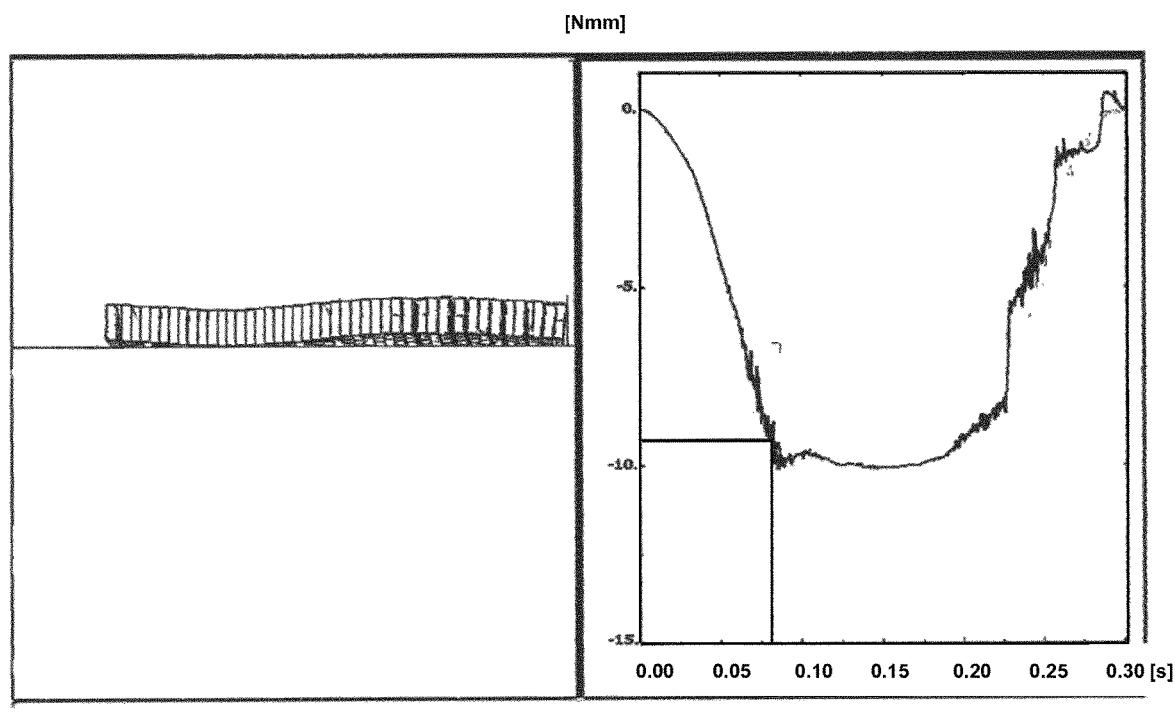
Figure 11C:
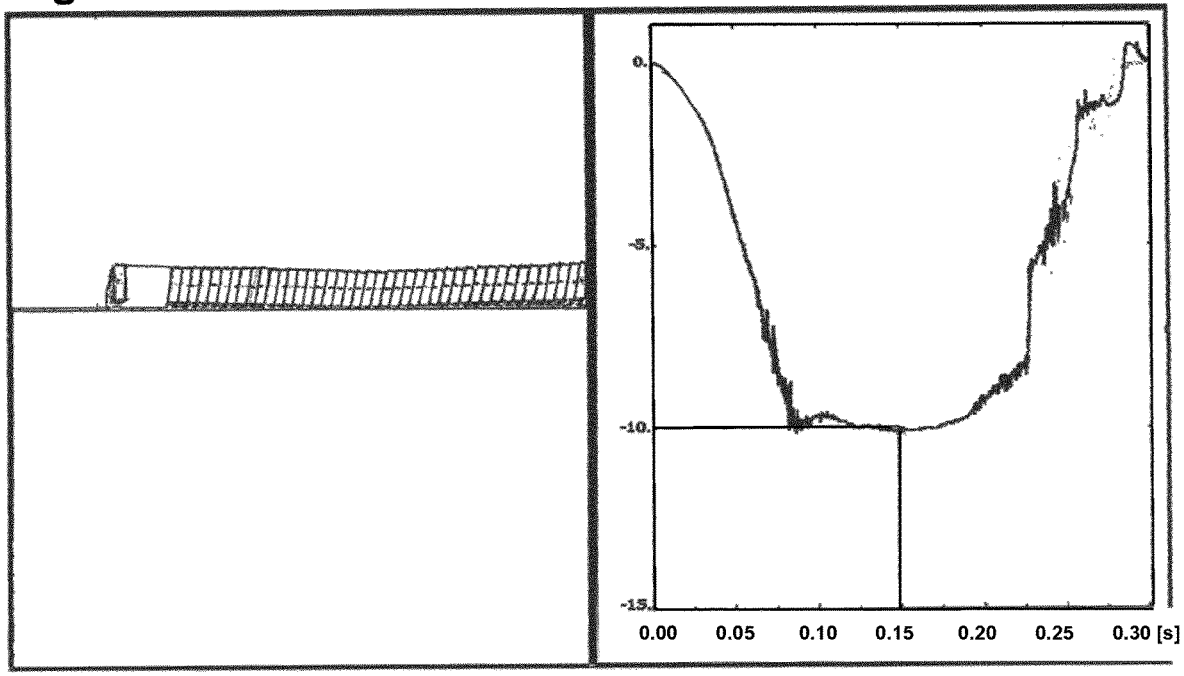

FIGS. 11A-11C show screenshots for a computerized finite element analysis of a helical coil wound from a wire with a rectangular cross-section. More specifically, the graph part to the right in the figures show on the vertical axis the torque provided by the spring as it is twisted and subsequently relaxed as a function of time. To minimize noise in the simulation from dynamic effects the deformation in degrees per time unit is not constant but accelerated/decelerated at begin respectively end of simulation.

The graph part is the same in the three figures. To the left in the figures simulations of how the spring will twist and tilt as it is strained. FIG. 11A shows the spring in the initial condition with no torque applied, FIG. 11B shows how the spring has twisted and start to tilt as a torque of 9 Nmm is applied, this providing a "shoulder" on the graph, and FIG. 11C shows how the spring coils has almost uniformly tilted with a torque of 10 Nmm applied. The corresponding point on the graph is indicated in each graph. To assure that the wire along the length of the spring initially will tilt in the same direction the spring may fully or partly comprise a "pre-tilted" wire, this assuring that the wire subsequently will tilt (further) in the desired direction. Further, pre-tilting will facilitate initial tilting and may thus result in a "rounder" shoulder. The pre-tilting can be introduced by the process equipment when the rectangular wire is formed into a helical spring.

Figure 12:
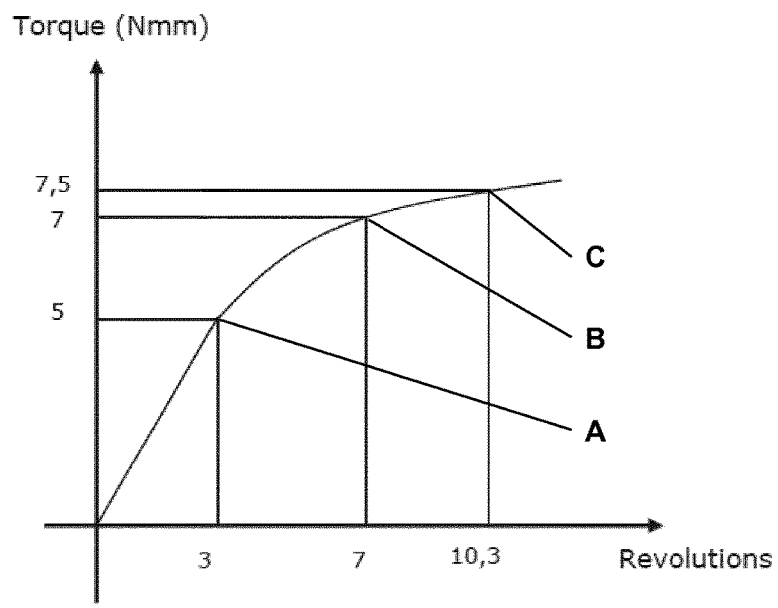
FIG. 12 shows an idealized diagram the torque produced as a function of the number of revolutions a model spring is twisted.

Based on the above findings FIG. 12 shows in an idealized diagram the torque produced as a function of the number of revolutions a spring is twisted. The spring parameters, e.g. number of windings, diameter and cross-sectional dimensions, have been chosen corresponding to an application in a drug delivery device of the type described above with reference to FIGS. 2-10. As appears, between 7 and 10.3 revolutions the model spring produces a near-constant torque of 7-7.5 Nmm, the 7 revolutions corresponding to a pre-strained spring in the initial zero condition for the drug delivery device and the 10.3 revolutions approximately corresponds to a maximal set dose, e.g. 80 units of insulin for a 100 IU/ml insulin formulation. More specifically, until point A with the spring wound 3 revolutions the spring characteristic is essentially linear. The cross section (or the wire plane) of the spring wire is still essentially perpendicular to the centre axis of the spring corresponding to FIG. 11A. In point B at 7 revolutions the cross section of the spring wire has started to tilt and thus the linear torque characteristic tendency has started to decrease. In point C at 10.3 revolutions the cross section of the spring wire has tilted further as shown in FIG. 11C and the torque characteristic is now almost constant.

Turning to the formulas on which the above-described simulation is based, the spring characteristic (torque as a function of angular deformation in degrees) can be expressed as:

$$k = (\pi * E)/(180 * n * D), \text{ where} \quad (1)$$

E=Young's modulus, n=number of spring coils in relaxed condition, D=spring coil diameter in relaxed condition, all of which are constant, as well as I=second moment of inertia which is variable. I is the variable value in the spring characteristic as the cross section of the wire is tilting. The second moment of inertia can be expressed as:

$$I = (t * h)/12 * (h^{2} * \cos(\alpha)^{2} + t^{2} * \sin(\alpha)^{2}); t, h \text{ and } \alpha \text{ as illustrated in FIG. 13.} \quad (2)$$

As appears from FIG. 13, α corresponds to the tilting angle between the initially defined wire plane and spring reference plane.

Figure 14:
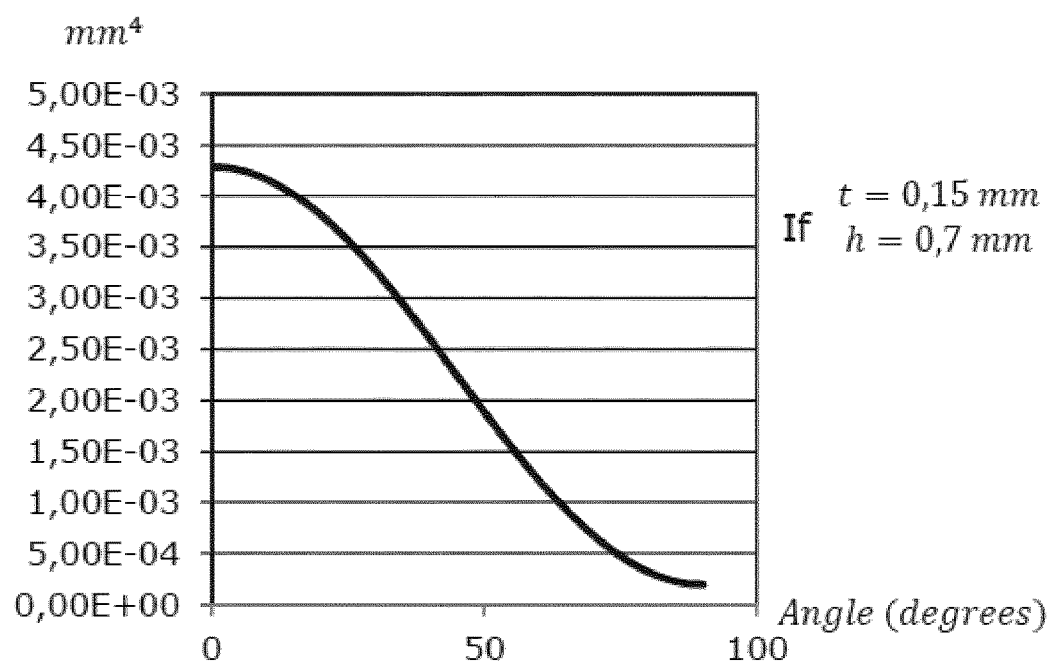
FIG. 14 shows the variation of the second moment of inertia for a spring wire as it is tilted from its initial state.

For t=0.15 mm and h=0.7 mm the second moment of inertia I is shown in FIG. 14 as a function of α. As appears, even for smaller angels the second moment of inertia I for the exemplary rectangular wire varies significantly, this resulting in the above-described almost-constant torque characteristic in the specified working range for a torsion drive spring arranged in a drug delivery device of the above-described type.

In the above description of different embodiments of a torsion spring comprising rectangular wire, a number of parameters influencing the spring torque characteristics have been addressed. As appears, for a given torsion spring a large number of design options are at hand, e.g. the spring may be manufactured fully or partly from rectangular wire, the wire may be operated from a pre-strained state, the wire may be operated from a pre-strained state in which at least a portion of the wire has been tilted (i.e. strained pre-tilt), the wire may be wound with at least portions of the wire being pre-tilted (i.e. unstrained pre-tilt), the wire may be wound with one or more open sections, the wire may be wound with non-constant diameter, the wire may have a given aspect ratio, e.g. larger than 1.5, larger than 2 or larger than 3, and the wire may be arranged to engage at least in part an inner support surface as the diameter of the spring is reduced during straining. All of these design parameters may be utilized to realize a torsion spring having a desired torque characteristic for a given device within a given operational range of straining.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising or adapted to receive a drug-filled cartridge, comprising:
   a housing,
   a piston rod adapted to engage and axially displace a piston in a loaded cartridge in a distal direction to thereby expel a dose of drug from the cartridge,
   a transmission member defining an axis,
   a drive spring coupled to the transmission member,
   a drive member in engagement with the piston rod and adapted to be rotated by the transmission member to thereby move the piston rod distally during expelling,
   a dose setting structure allowing a user to simultaneously set a dose amount to be expelled and strain the drive spring correspondingly by rotation of the transmission member, the dose setting structure comprising a dose setting member which during dose setting is rotationally coupled to the transmission member and adapted to rotate in a first direction to set a dose,
   a releasable ratchet mechanism allowing the dose setting member to be rotated in the first direction to a set rotational position,
   a releasable clutch mechanism adapted to rotationally lock the drive member relative to the housing during dose setting,
   a release structure actuatable between a dose setting mode and an expelling mode, wherein the clutch mechanism comprises:
   a relative to the housing axially non-moveable clutch member, and
   a relative to the housing rotationally non-moveable locking member,
   wherein during dose setting and dose expelling the clutch member is rotationally locked to the drive member,
   wherein the transmission member is actuatable between a dose setting state in which it is allowed to rotate relative to the clutch member, and an expelling state in which it is rotationally coupled to the clutch member,
   wherein the transmission member and the locking member are moved axially when actuated between the dose setting state and the expelling state, and wherein the transmission member and the locking member are axially locked but rotationally free relative to each other,
   wherein the locking member is actuatable between a dose setting state in which it is in rotationally locked engagement with the clutch member, and an expelling state in which it is rotationally decoupled from the clutch member,
   wherein, when the release structure is actuated from the dose setting mode to the expelling mode:
   the transmission member is actuated from its dose setting state to its expelling state,
   the locking member is actuated from its dose setting state to its expelling state, and
   the ratchet mechanism is released,
   whereby the strained drive spring is allowed to rotate the transmission member and the drive member and thereby move the piston rod distally.

2. A drug delivery device as in claim 1, wherein:
   the locking member in the dose setting state is in splined engagement with the clutch member, and
   the transmission member in the expelling state is in splined engagement with the clutch member.

3. A drug delivery device as in claim 1, wherein the clutch member is coupled to the housing via a uni-directional ratchet mechanism.

4. A drug delivery device as in claim 1, wherein the transmission member has at least partly engaged the clutch member before the locking member has been actuated to its expelling state.

5. A drug delivery device as in claim 1, comprising a cartridge holder coupled to the housing and adapted to receive and hold a cartridge, and a coupling mechanism allowing the piston rod to be moved in a proximal direction, this allowing a new cartridge to be received.

6. A drug delivery device as in claim 5, wherein the coupling mechanism can be actuated between:
   (i) an operational state in which the piston rod can be moved in the distal direction by rotation of the clutch member, and (ii) a loading state in which the piston rod can be moved in the proximal direction.

7. A drug delivery device as in claim 5, wherein the drive member is actuatable between:
   (i) an operational state in which the drive member is rotationally locked to the clutch member, and
   (ii) a loading state in which the drive member is rotationally decoupled from the clutch member, this allowing the drive member to rotate as the piston rod is moved in the proximal direction.

8. A drug delivery device as in claim 7, wherein the drive member is moved axially when actuated between the operational state and the loading state.

9. A drug delivery device as in claim 5, wherein the coupling mechanism comprises a coupling member adapted to engage a proximal end portion of a cartridge, the coupling member being moveable between:
   (i) a distal loading position in which the piston rod can be moved in the proximal direction, and
   (ii) a proximal operational position in which the piston rod can be moved in the distal direction by rotation of the clutch member.

10. A drug delivery device as in claim 8, wherein the coupling mechanism comprises a coupling member adapted to engage a proximal end portion of a cartridge, the coupling member being moveable axially between:
    (i) a distal loading position in which the piston rod can be moved in the proximal direction, and
    (ii) a proximal operational position in which the piston rod can be moved in the distal direction by rotation of the clutch member,
    wherein the coupling member and the drive member are axially locked but rotationally free relative to each other.

11. A drug delivery device as in claim 6, the cartridge holder being of the front-loaded type actuatable between:
    (i) a receiving state in which a cartridge can be inserted and received in a proximal direction, and
    (ii) a holding state in which an inserted cartridge is held in an operational position.

12. A drug delivery device as in claim 11, wherein the coupling mechanism is actuated between the loading state and the operational state when the cartridge holder is actuated between the receiving state and the holding state with a mounted cartridge.

13. A drug delivery device as in claim 1, further comprising:
    dose logging circuitry adapted to determine an amount of expelled drug, the determination comprising determining, directly or indirectly, the amount of rotation of the transmission member relative to the housing during expelling of an amount of drug.

* * * * *